(12) United States Patent
Hajduch et al.

(10) Patent No.: US 7,749,988 B2
(45) Date of Patent: Jul. 6, 2010

(54) TRITERPENOID DERIVATIVES

(75) Inventors: Marian Hajduch, Olomouc (CZ); Jan Sarek, Ostrava-Poruba (CZ)

(73) Assignees: Univerzita Palackeho V Olomouci, Olomouc (CZ); Univerzita Karlova V Praze, Prague (CZ)

( * ) Notice: Subject to any disclaimer, the term of this patent is extended or adjusted under 35 U.S.C. 154(b) by 1055 days.

(21) Appl. No.: 11/378,228

(22) Filed: Mar. 17, 2006

(65) Prior Publication Data

US 2006/0160890 A1    Jul. 20, 2006

Related U.S. Application Data

(63) Continuation of application No. 10/296,457, filed as application No. PCT/GB01/02313 on May 23, 2001, now Pat. No. 7,041,701.

(30) Foreign Application Priority Data

May 23, 2000    (GB) ................................. 0012526.0

(51) Int. Cl.
*A61K 31/585*    (2006.01)
*C07J 53/00*    (2006.01)

(52) U.S. Cl. ...................................... 514/175; 552/510

(58) Field of Classification Search ................. 514/510, 514/175; 560/257; 552/510
See application file for complete search history.

(56) References Cited

OTHER PUBLICATIONS

Klinotova et al., "Oxidation of 3beta,28-diacetoxy-18-lupen-21-one with peroxy acids: A way to des-E-lupane derivatives." Collect. Czech. Chem. Commun., vol. 58, pp. 2505-2516, 1993.*
Database Crossfire Beilstein Online Accession No. 5852757. "Oxidation of 3?,28-Diacetoxy-18-Lupen-21-One with Peroxy Acids: A Way to Des-E-Lupane Derivatives" 1993.
Database Crossfire Beilstein Online Accession No. 5714369. "Retro-Michael Reaction of 28-Methoxy-18, 19-Secoulupane-18, 19-Dione Derivatives." 1992.

* cited by examiner

*Primary Examiner*—Barbara P Badio
(74) *Attorney, Agent, or Firm*—Lahive & Cockfield, LLP; Cynthia L. Kanik; Brian C. Trinque

(57) ABSTRACT

The present invention relates to the use of a compound of formula (I), or a pharmaceutically acceptable salt thereof, in therapy. Prefereably, the compound may be used for treating a patient suffering from leukaemia, cancer or other proliferative disorder. A further embodiment relates to the use of a compound of formula (I) in an assay for detecting the phosphorylation and acetylation state of cellular substrates. The present invention also relates to novel compounds of formula (Ia).

18 Claims, 8 Drawing Sheets

TRITERPENOID DERIVATIVES

RELATED APPLICATIONS

This application is a continuation application of U.S. Ser. No. 10/296,457, filed Nov. 25, 2002; which is a 35 U.S.C. §371 filing of International Application Number PCT/GB01/02313, filed 23 May 2001, which claims priority to Great Britain Publication 0012526.0, filed 23 May 2000 in Great Britain. The contents of all of the aforementioned applications are hereby incorporated by reference in their entirety.

BACKGROUND TO THE INVENTION

The present invention relates to the therapeutic use and the biological activity of triterpenoid derivatives. The invention further relates to novel triterpenoid derivatives.

To date, the prior art has primarily focussed on compounds that are capable of regulating the cell cycle by virtue of inhibiting cyclin dependent kinases (CDKs). Examples of such compounds include butyrolactone I, flavopiridol, bohemin, olomoucine, roscovitine, purvanalol and indarubicine.

There is considerable support in the literature for the hypothesis that CDKs and their regulatory proteins play a significant role in the development of human tumours. Thus, in many tumours a temporal abnormal expression or activity of CDKs has been observed, together with a major deregulation of protein inhibitors (mutations, deletions). This results in the activation of CDKs and consequently in defective regulation of the G1/S transition. Unlike normal cells, tumour cells do not arrest in G1, and since they become independent of growth factors, they pass the G1 restriction point and enter the S phase very rapidly.

In contrast to the prior art, the present invention relates to compounds which are anti-proliferative, but which are believed to operate via a mechanism other than CDK inhibition.

The Gi/S transition of the mammalian cell cycle is tightly regulated by the retinoblastoma protein (pRb). Retinoblastoma gene mutations or deletions predispose individuals to familiar retinoblastoma and other types of cancers. The pRb protein is a docking protein, which in hypophosphorylated form has the capacity to bind and thus to inactivate S-phase transcription factors such as DP-1 and E2F. However, following phosphorylation by $G_1$/S cyclin-dependent kinases (CDKs) (CDK4/cyclin D1-D3, CDK6/cyclin D1-D3, CDK2/cyclin A), hyperphosphorylated pRb releases the transcription factors and S phase is initiated. Within the S phase, the pRb protein phosphorylation is maintained by the activity of CDK2/cyclin E complexes. Thus, hyperphosphorylation of the pRb protein plays a key role in the molecular pathology of cancer cells with altered CDK activity.

The present invention relates to the use of triterpenoid compounds derived from the natural products betulin and betulinic acid (BA) as shown in formula (A). The compounds of the present invention are referred to hereinafter as betulinines.

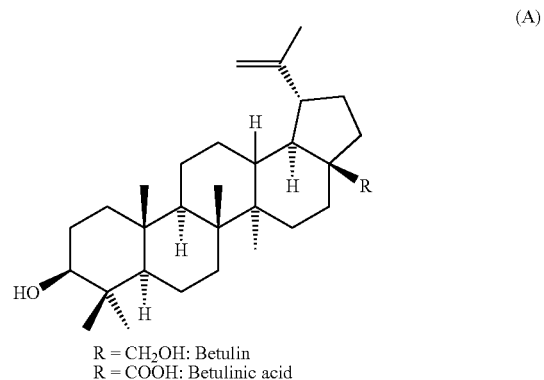

(A)

R = CH$_2$OH: Betulin
R = COOH: Betulinic acid

With regard to their biological and therapeutic activity, the compounds disclosed herein are believed to be of specific benefit in the treatment of proliferative diseases such as cancers and leukaemias.

Several of the compounds suitable for use in the present invention are already known in the art, for example those disclosed in Ber. Dtsch. Chem. Ges. 55, 2332 (1922), Schluze, H. et al; Acta Chem. Scand., B 29, 139 (1975), Suokas E. et al; Collect. Czech. Chem. Commun. 56, 2936 (1991), Sejbal J. et al; Collect. Czech. Chem. Commun. 64, 329 (1999), Klinotová et al; Indian. J. Chem., Sect. B 34, 624 (1995), Dinda B. et al; Chem. Listy 91, 1005 (1997), Sarek J. et al. However, these disclosures do not include any indication as to possible biological activity of such compounds.

A first aspect of the present invention relates to the use of a compound of formula I, or a pharmaceutically acceptable salt thereof, in therapy,

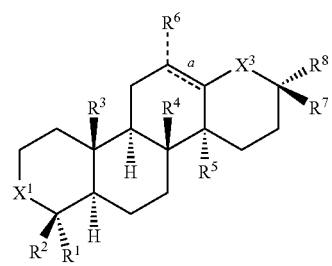

I wherein:
  $X^1$ is C=O, C=NOR$^{1a}$, CHOR$^{1a}$, CHOCOR$^{1a}$, CHOCOY-Hal, CHOC(O)OR$^9$, CHOC(O)OR$^{1a}$, CHOC(O)OR$^{10}$, and Hal is Br, Cl, I, F;
  $X^3$ is C=O, CHOR$^{1b}$, CHOCOR$^{1b}$, or $X^3$ and R$^8$ together are CHOCOCH$_2$ and form a spirolactone;
  $R^{1-5}$ are each independently H or lower alkyl;
  $R^6$ is H or absent if "a" is a double bond;
  $R^7$ is H, COOR$^{1c}$, YOCOR$^{1c}$, COOYOCOR$^{1e}$, YCOOR$^{1e}$;
  $R^8$ is H, COOR$^{1d}$, YCOOR$^{1d}$, YCOOR$^{10}$, YCOHal, COOYOCOR$^{1d}$, CH$_2$OR$^{1d}$, CH$_2$COCOR$^{1d}$, COCOCOR$^{1d}$
  or R$^7$ and R$^8$ together are =CH$_2$ or CH$_2$OCOCH$_2$;
  $R^9$ is an OH-substituted alkyl group, an ether group or a cyclic ether;
  $R^{10}$ is lower alkyl substituted by Hal
  "a" is a double bond or a single bond
  and wherein Y=(CH$_2$)$_n$ n=0 to 5;
$R^{1a-1d}$ are the same or different groups of $R^1$.

In a preferred aspect, the invention relates to the use of a compound of formula I, or a pharmaceutically acceptable salt thereof for treating a patient suffering from leukaemia, cancer or other proliferative disorder.

A second aspect of the present invention relates to novel betulinines of structural formula Ia, or pharmaceutically acceptable salts, thereof;

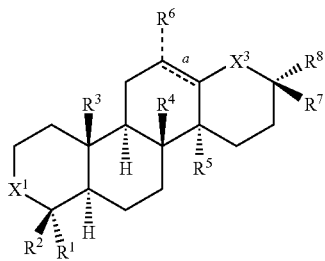

Ia wherein:
$X^1$ is C=O, C=NOR$^{1a}$, CHOR$^{1a}$, CHOCOR$^{1a}$, CHOCOY-Hal, CHOC(O)OR$^9$, CHOC(O)OR$^{1a}$, CHOC(O)OR$^{10}$, and Hal is Br, Cl, I, F;
$X^3$ is C=O, CHOR$^{1b}$, CHOCOR$^{1b}$, or $X^3$ and $X^8$ together are CHOCOCH$_2$ and form a spirolactone;
$R^{1-5}$ are each independently H or lower alkyl;
$R^6$ is H or absent if "a" is a double bond;
$R^7$ is H, COOR$^{1c}$, YOCOR$^{1c}$, COOYOCOR$^{1e}$, YCOOR$^{1e}$;
$R^8$ is H, COOR$^{1d}$, YCOOR$^{1d}$, YCOOR$^{10}$, YCOHal, COOYOCOR$^{1d}$, CH$_2$OR$^{1d}$, CH$_2$COCOR$^{1d}$, COCOCOR$^{1d}$
or $R^7$ and $R^8$ together are =CH$_2$ or CH$_2$OCOCH$_2$;
$R^9$ is an OH-substituted allyl group, an ether group or a cyclic ether,
$R^{10}$ is lower alkyl substituted by Hal
"a" is a double bond or a single bond
and wherein Y=(CH$_2$)n
n=0 to 5;
$R^{1a-1d}$ are the same or different groups of $R^1$ with the proviso that
(i) when $X^1$ is CHOAc, $X^3$ is C=O, "a" is single bond, $R^{1-5}$ are Me, $R^6$ is H;
when $R^7$ is CH$_2$OAc, $R^8$ is other than COOH, CH$_2$COCOPr$^i$, COCOCOPr$^i$, CH$_2$COOH, or CH$_2$CH$_2$CO$^i$Pr;
when $R^7$ is CO$_2$Me, $R^8$ is other than CH$_2$CH$_2$COCH(CH$_3$)$_2$;

when $R^7$ is H, $R^8$ is other than H, CH$_2$COOMe, CH$_2$COOH or CH$_2$CH$_2$COPr$^i$; and
(ii) when $X^1$ is CHOH, $X^3$ is C=O, "a" is a single bond, $R^{1-5}$ are Me, and $R^6$ is H;
when $R^7$ is H, $R^8$ is other than H, CH$_2$COOH, CH$_2$CH$_2$COCH(CH$_3$)$_2$ or CH$_2$COOMe;
when $R^7$ is CH$_2$OAc, $R^8$ is other than CH$_2$COOH;
or a pharmaceutically acceptable salt thereof.

As used herein, the term lower alkyl means a linear or branched chain alkyl group containing from 1 to 6 carbon atoms, including methyl, ethyl, propyl, isopropyl, butyl, isobutyl, tertiary butyl.

DESCRIPTION OF THE PREFERRED EMBODIMENTS

Within the options provided for the groups $X^1$, $X^3$ and $R^{1-8}$ of formula I, the following options are preferred;
Preferably,
$X^1$ is CHOR$^{1a}$, CHOCOR$^{1a}$ or CHOCOY-Hal; and
$R^8$ is H, COOR$^{1d}$, YCOOR$^{1d}$, COOYOCOR$^{1d}$, CH$_2$OR$^{1d}$, CH$_2$COCOR$^{1d}$ or COCOCOR$^{1d}$.

In a more preferred embodiment, $R^{2-5}$ are all methyl and $R^1$ is as defined below for the relevant group $R^{1a-1d}$;
$X^1$ is —CHOCOCH$_2$Cl; or
—CHOR$^{1a}$ or CHOCOR$^{1a}$, wherein R$^{1a}$ is H and methyl respectively,
$X^3$ is C=O, CHOH or CHOAc;
$R^7$ is H, COOH COOMe, CH$_2$OAc, COOYOCOR$^{1e}$ or YCOOR$^{1e}$ where
Y is CH$_2$ and R$^{1e}$ is C$_{1-4}$ alkyl;
$R^8$ is —COOR$^{1d}$, wherein R$^{1d}$ is H or methyl;
—YCOOR$^{1d}$, wherein Y is CH$_2$ and R$^{1d}$ is H, methyl or ethyl;
—COOYOCOR$^{1d}$, wherein Y is CH$_2$ and R$^{1d}$ is C$_{1-4}$ alkyl;
—CH$_2$OR$^{1d}$, wherein R$^{1d}$ is C$_{1-4}$ alkyl;
—CH$_2$COCOR$^{1d}$ or COCOCOR$^{1d}$, wherein R$^{1d}$ is C$_{1-4}$ alkyl;

Of the preferred definitions provided above, it is preferable that;
$R^8$ is —COOYOCOR$^{1d}$, wherein Y is CH$_2$ and R$^{1d}$ is methyl or butyl;
—CH$_2$OR$^{1d}$, wherein R$^{1d}$ is methyl or ethyl;
—CH$_2$COCOR$^{1d}$ or COCOCOR$_{1d}$, wherein R$^{1d}$ is propyl; and
$R^7$ is COOYOCOR$^{1e}$ or YCOOR$^{1e}$ where Y is CH$_2$ and R$^{1e}$ is methyl or butyl.

In a preferred embodiment, "a" is a single bond and R$^6$ is H.
In a more preferred embodiment of the first aspect of the invention, the compounds of use are selected from those shown in Table 1 below.

TABLE 1

| No. | $X^1$ | $R^1$ | $X^3$ | a | $R^{2-5}$ | $R^6$ | $R^7$ | $R^8$ |
|---|---|---|---|---|---|---|---|---|
| I.1 | CHOAc | CH$_3$ | C=O | single | Me | H | CH$_2$OAc | CH$_2$COCOPr$^i$ |
| I.2 | CHOAc | CH$_3$ | C=O | single | Me | H | CH$_2$OAc | COCOCOPr$^i$ |
| I.3 | CHOAc | CH$_3$ | C=O | single | Me | H | CH$_2$OAc | COOH |
| I.4 | CHOAc | CH$_3$ | C=O | single | Me | H | CH$_2$OAc | COOMe |
| I.5 | CHOAc | CH$_3$ | C=O | single | Me | H | H | H |
| I.6 | CHOAc | CH$_3$ | C=O | single | Me | H | H | CH$_2$COOH |
| I.7 | CHOAc | CH$_3$ | C=O | single | Me | H | H | CH$_2$OEt |
| I.8 | CHOAc | CH$_3$ | CHOH | single | Me | H | CH$_2$OAc | COOH |
| I.9 | CHOAc | CH$_3$ | C=O | double | Me | absent | CH$_2$OAc | COOMe |
| I.10 | CHOAc | CH$_3$ | CHOH | single | Me | H | $R^7$ and $R^8$ together: =CH$_2$ | |
| I.11 | CHOAc | CH$_3$ | CHOAc | single | Me | H | CH$_2$OAc | COOMe |

TABLE 1-continued

| No. | X¹ | R¹ | X³ | a | R$^{2-5}$ | R⁶ | R⁷ | R⁸ |
|---|---|---|---|---|---|---|---|---|
| I.12 | CHOAc | CH₃ | C=O | single | Me | H | COOMe | CH₂COCOPr$^r$ |
| I.13 | CHOAc | CH₃ | C=O | single | Me | H | COOMe | COOH |
| I.14 | CHOAc | CH₃ | C=O | single | Me | H | COOMe | CH₂COOH |
| I.15 | CHOAc | CH₃ | CHOH | single | Me | H | CH₂OAc | COOCH₂OCOBu$^t$ |
| I.16 | CHOAc | CH₃ | CHOH | single | Me | H | CH₂OAc | COOMe |
| I.17 | CHOAc | CH₃ | C=O | single | Me | H | CH₂OAc | CH₂COOH |
| I.18 | CHOAc | CH₃ | C=O | single | Me | H | CH₂OAc | COOCH₂OCOBu$^t$ |
| I.19 | CHOAc | CH₃ | C=O | single | Me | H | CH₂OAc | COOCH₂OCOMe |
| I.20 | CHOAc | CH₃ | C=O | double | Me | absent | CH₂OAc | COOCH₂OCOBu$^t$ |
| I.21 | CHOAc | CH₃ | C=O | double | Me | absent | CH₂OAc | COOCH₂OCOMe |
| I.22 | CHOAc | CH₃ | C=O | double | Me | absent | CH₂OAc | COOH |
| I.24 | CHOAc | CH₃ | C=O | single | Me | H | R⁷ and R⁸ together: =CH₂ | |
| I.26 | CHOH | H | C=O | single | Me | H | CH₂OAc | COOH |
| I.27 | CHOH | H | C=O | double | Me | absent | CH₂OAc | COOMe |
| I.28 | CHOAc | CH₃ | C=O | single | Me | H | COOCH₂OCOMe | CH₂COCOPr$^r$ |
| I.29 | CHOAc | CH₃ | C=O | single | Me | H | COOCH₂OCOBu$^t$ | CH₂COCOPr$^r$ |
| I.30 | CHOAc | CH₃ | C=O | single | Me | H | from R⁷ to R⁸: CH₂OC(O)CH₂ | |
| I.31 | CHOAc | CH₃ | CHOAc | single | Me | H | CH₂OAc | COOH |
| I.32 | CHOAc | CH₃ | CHOAc | single | Me | H | CH₂OAc | COOCH₂OCOBu$^t$ |
| I.33 | CHOAc | CH₃ | CHOH | single | Me | H | CH₂OAc | COOMe |
| I.34 | CHOAc | CH₃ | CHOAc | single | Me | H | CH₂OAc | COOMe |
| I.35 | CHOAc | CH₃ | CHOH | single | Me | H | CH₂OAc | COOCH₂OCOBu$^t$ |
| I.36 | CHOAc | CH₃ | CHOAc | single | Me | H | CH₂OAc | COOCH₂OCOBu$^t$ |
| I.37 | CHOAc | CH₃ | C=O | single | Me | H | CH₂OAc | COOMe |
| I.38 | CHOAc | CH₃ | C=O | single | Me | H | H | CH₂COOMe |
| I.39 | CHOAc | CH₃ | C=O | single | Me | H | COOMe | CH₂COOMe |
| I.40 | CHOAc | CH₃ | C=O | single | Me | H | COOCH₂OCOBu$^t$ | CH₂COOMe |
| I.41 | CHOAc | CH₃ | C=O | single | Me | H | COOCH₂OCOMe | CH₂COOMe |
| I.42 | CHOAc | CH₃ | CHOH | single | Me | H | R⁷ and R⁸ together: =CH₂ | |
| I.43 | CHOAc | CH₃ | CHOH | single | Me | H | H | H |
| I.44 | CHOCOCH₂Cl | CH₃ | C=O | single | Me | H | CH₂OAc | COOH |
| I.45 | CHOAc | CH₃ | CHOH | single | Me | H | CH₂OAc | COOH |
| I.46 | CHOAc | CH₃ | CHOAc | single | Me | H | CH₂OAc | COOH |
| I.47 | CHOAc | CH₃ | CHOAc | single | Me | H | R⁷ and R⁸ together: =CH₂ | |
| I.48 | CHOAc | CH₃ | CHOAc | single | Me | H | H | H |
| I.49 | CHOH | CH₃ | C=O | single | Me | H | H | CH₂COOH |
| I.50 | CHOH | CH₃ | C=O | single | Me | H | H | CH₂COOMe |
| I.51 | CHOH | CH₃ | CHOH | single | Me | H | H | CH₂COOMe |
| I.52 | CHOAc | CH₃ | CHOH | single | Me | H | H | CH₂COOMe |
| I.53 | CHOH | CH₃ | CHOH | single | Me | H | CH₂COOMe | H |
| I.54 | CHOAc | CH₃ | CHOAc | single | Me | H | CH₂COOMe | H |
| I.55 | CHOAc | CH₃ | ① | single | Me | H | H | ① |
| I.56 | CHOH | CH₃ | ① | single | Me | H | H | ① |
| I.57 | CHOH | CH₃ | C=O | single | Me | H | CH₂OAc | COOH |
| I.58 | CHOAc | CH₃ | C=O | single | Me | H | CH₂OAc | COF | where:
① means cyclic five-membered spirolactone from X³ to R⁸: OCOCH₂

In a most preferred embodiment, the compound is selected from;

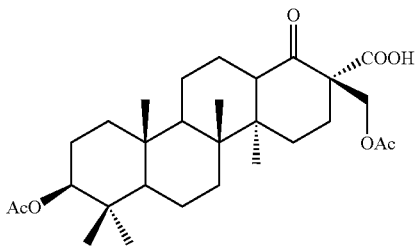

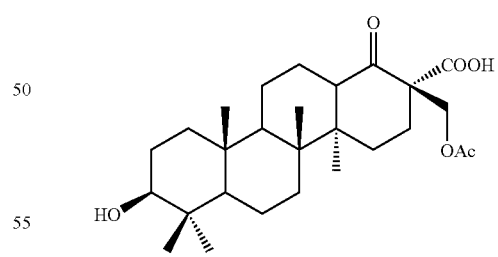

In respect of the second aspect of the invention, the preferred embodiments regarding the compounds are identical to those given above for the first aspect with application of the proviso of formula Ia.

The most preferred compounds of the second aspect are those in Table 1a below.

TABLE 1a

| No. | $X^1$ | $R^1$ | $X^3$ | a | $R^{2-5}$ | $R^6$ | $R^7$ | $R^8$ |
|---|---|---|---|---|---|---|---|---|
| I.4 | CHOAc | $CH_3$ | C=O | single | Me | H | $CH_2OAc$ | COOMe |
| I.7 | CHOAc | $CH_3$ | C=O | single | Me | H | H | $CH_2OEt$ |
| I.8 | CHOAc | $CH_3$ | CHOH | single | Me | H | $CH_2OAc$ | COOH |
| I.9 | CHOAc | $CH_3$ | C=O | double | Me | absent | $CH_2OAc$ | COOMe |
| I.10 | CHOAc | $CH_3$ | CHOH | single | Me | H | $R^7$ and $R^8$ together: =$CH_2$ | |
| I.11 | CHOAc | $CH_3$ | CHOAc | single | Me | H | $CH_2OAc$ | COOMe |
| I.12 | CHOAc | $CH_3$ | C=O | single | Me | H | COOMe | $CH_2COCOPr^i$ |
| I.13 | CHOAc | $CH_3$ | C=O | single | Me | H | COOMe | COOH |
| I.14 | CHOAc | $CH_3$ | C=O | single | Me | H | COOMe | $CH_2COOH$ |
| I.15 | CHOAc | $CH_3$ | CHOH | single | Me | H | $CH_2OAc$ | $COOCH_2OCOBu^t$ |
| I.16 | CHOAc | $CH_3$ | CHOH | single | Me | H | $CH_2OAc$ | COOMe |
| I.18 | CHOAc | $CH_3$ | C=O | single | Me | H | $CH_2OAc$ | $COOCH_2OCOBu^t$ |
| I.19 | CHOAc | $CH_3$ | C=O | single | Me | H | $CH_2OAc$ | $COOCH_2OCOMe$ |
| I.20 | CHOAc | $CH_3$ | C=O | double | Me | absent | $CH_2OAc$ | $COOCH_2OCOBu^t$ |
| I.21 | CHOAc | $CH_3$ | C=O | double | Me | absent | $CH_2OAc$ | $COOCH_2OCOMe$ |
| I.22 | CHOAc | $CH_3$ | C=O | double | Me | absent | $CH_2OAc$ | COOH |
| I.24 | CHOAc | $CH_3$ | C=O | single | Me | H | $R^7$ and $R^8$ together: =$CH_2$ | |
| I.26 | CHOH | H | C=O | single | Me | H | $CH_2OAc$ | COOH |
| I.27 | CHOH | H | C=O | double | Me | absent | $CH_2OAc$ | COOMe |
| I.28 | CHOAc | $CH_3$ | C=O | single | Me | H | $COOCH_2OCOMe$ | $CH_2COCOPr^i$ |
| I.29 | CHOAc | $CH_3$ | C=O | single | Me | H | $COOCH_2OCOBu^t$ | $CH_2COCOPr^i$ |
| I.30 | CHOAc | $CH_3$ | C=O | single | Me | H | from $R^7$ to $R^8$: $CH_2OC(O)CH_2$ | |
| I.31 | CHOAc | $CH_3$ | CHOAc | single | Me | H | $CH_2OAc$ | COOH |
| I.32 | CHOAc | $CH_3$ | CHOAc | single | Me | H | $CH_2OAc$ | $COOCH_2OCOBu^t$ |
| I.33 | CHOAc | $CH_3$ | CHOH | single | Me | H | $CH_2OAc$ | COOMe |
| I.34 | CHOAc | $CH_3$ | CHOAc | single | Me | H | $CH_2OAc$ | COOMe |
| I.35 | CHOAc | $CH_3$ | CHOH | single | Me | H | $CH_2OAc$ | $COOCH_2OCOBu^t$ |
| I.36 | CHOAc | $CH_3$ | CHOAc | single | Me | H | $CH_2OAc$ | $COOCH_2OCOBu^t$ |
| I.37 | CHOAc | $CH_3$ | C=O | single | Me | H | $CH_2OAc$ | COOMe |
| I.39 | CHOAc | $CH_3$ | C=O | single | Me | H | COOMe | $CH_2COOMe$ |
| I.40 | CHOAc | $CH_3$ | C=O | single | Me | H | $COOCH_2OCOBu^t$ | $CH_2COOMe$ |
| I.41 | CHOAc | $CH_3$ | C=O | single | Me | H | $COOCH_2OCOMe$ | $CH_2COOMe$ |
| I.42 | CHOAc | $CH_3$ | CHOH | single | Me | H | $R^7$ and $R^8$ together: =$CH_2$ | |
| I.43 | CHOAc | $CH_3$ | CHOH | single | Me | H | H | H |
| I.44 | $CHOCOCH_2Cl$ | $CH_3$ | C=O | single | Me | H | $CH_2OAc$ | COOH |
| I.45 | CHOAc | $CH_3$ | CHOH | single | Me | H | $CH_2OAc$ | COOH |
| I.46 | CHOAc | $CH_3$ | CHOAc | single | Me | H | $CH_2OAc$ | COOH |
| I.47 | CHOAc | $CH_3$ | CHOAc | single | Me | H | $R^7$ and $R^8$ together: =$CH_2$ | |
| I.48 | CHOAc | $CH_3$ | CHOAc | single | Me | H | H | H |
| I.51 | CHOH | $CH_3$ | CHOH | single | Me | H | H | $CH_2COOMe$ |
| I.52 | CHOAc | $CH_3$ | CHOH | single | Me | H | H | $CH_2COOMe$ |
| I.53 | CHOH | $CH_3$ | CHOH | single | Me | H | $CH_2COOMe$ | H |
| I.54 | CHOAc | $CH_3$ | CHOAc | single | Me | H | $CH_2COOMe$ | H |
| I.55 | CHOAc | $CH_3$ | ① | single | Me | H | H | ① |
| I.56 | CHOH | $CH_3$ | ① | single | Me | H | H | ① |
| I.57 | CHOH | $CH_3$ | C=O | single | Me | H | $CH_2OAc$ | COOH |
| I.58 | CHOAc | $CH_3$ | C=O | single | Me | H | $CH_2OAc$ | COF | where:
① means cyclic five-membered spirolactone from $X^3$ to $R^8$: $OCOCH_2$

In respect of the invention as a whole, it is preferable that the proliferative disorder is cancer or leukaemia. In one embodiment, the cancer or leukaemia is p53, hormone and multidrug resistance independent. In another embodiment, the cancer or leukaemia is independent of Rb status.

More specifically, the present invention relates to a method of treating patients suffering from cancer by administering therapeutically effective amounts of a compound of formula I or pharmaceutically acceptable salts or esters thereof.

Without wishing to be bound by theory, preliminary studies suggest that rather than influencing the activity of cyclin dependent kinases, the compounds of the present invention appear to operate via an alternative mechanism. In particular, it is believed that the betulinines of the present invention may inhibit cell proliferation and induce cancer cell death in a manner which involves mainly post-translational modifications, namely the phosphorylation, of a key regulatory protein involved in cellular proliferation. More specifically, it is believed that the betulinines of the invention effect a change in the phosphorylation state of the Rb protein. Such a mechanism may be advantageous as it is thought that the compounds of the present invention may be capable of inhibiting cell proliferation in proliferating tumour tissue, but not in healthy tissue.

Thus, in a further embodiment the present invention relates to a method of treating a cancerous or leukaemic proliferative disease through effecting a change in the pRb protein phosphorylation state by the administration of a therapeutically effective amount of a compound of formula I or pharmaceutically acceptable salts or esters thereof.

The compounds of the present invention are also capable of inducing apoptosis (programmed cell death) in proliferative cells. Thus, in an additional embodiment, the present invention relates to a method of inducing cell death in proliferative cells comprising administering a therapeutically effective amount of a compound of formula I or pharmaceutically acceptable salts or esters thereof.

A further aspect of the present invention relates to use of betulinines of formula I as research chemicals and as compounds for clinical and/or laboratory diagnostics. More particularly, the invention relates to the use of betulinines as research chemicals for studying the phosphorylation/dephosphorylation processes of cellular substrates, cellular proliferation, purification of target molecules, and/or cell cycle studies.

The present invention therefore further relates to the use of a compound, of formula I in the preparation of a medicament for use in the treatment of a proliferative disease.

As used herein the phrase "preparation of a medicament" includes the use of a compound of formula I directly as the medicament in addition to its use in a screening programme for the identification of further anti-proliferative agents or in any stage of the manufacture of such a medicament.

Such a screening programme may for example include an assay for determining the phosphorylation state of cellular substrates and determining whether a candidate substance is capable of mimicking the activity of a betulinine of formula I.

Thus, in a further embodiment, the invention relates to the use of a compound of formula I or a pharmaceutically acceptable salt, crystal form, complex, hydrate, or hydrolysable ester thereof, in an assay for determining the phosphorylation state of cellular substrates, and optionally in the identification of candidate compounds that act in a similar manner.

Preferably, the cellular substrate, the phosphorylation state of which is being assayed is Rb protein.

The compounds of the first and second aspects of the present invention can be present as salts or esters, in particular pharmaceutically acceptable salts or esters.

Pharmaceutically acceptable salts of the product of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid, with benzoic acid; or with organic sulfonic acids, such as ($C_1$-$C_4$)-aryl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanalcohols of 1-12 carbon atoms which may be unsubstituted or substituted, e.g. by a halogen).

In all aspects of the present invention previously discussed, the invention includes, where appropriate all enantiomers and tautomers of compounds of formula I or Ia. The man skilled in the art will recognise compounds that possess optical properties (one or more chiral carbon atoms) or tautomeric characteristics. The corresponding enantiomers and/or tautomers may be isolated/prepared by methods known in the art.

The invention furthermore relates to the compounds of, or of use, in the present invention in their various crystalline forms, polymorphic forms and (an)hydrous forms. It is well established within the pharmaceutical industry that chemical compounds may be isolated in any of such forms by slightly varying the method of purification and or isolation from the solvents used in the synthetic preparation of such compounds.

The invention further includes the compounds of, or of use, in the present invention in prodrug form. Such prodrugs are generally compounds of formula I or Ia wherein one or more appropriate groups have been modified such that the modification is reversed upon administration to a human or mammalian subject. Such reversion is usually performed by an enzyme naturally present in such subject, though it is possible for a second agent to be administered together with such a prodrug in order to perform the reversion in vivo. Examples of such modifications include esters (for example, any of those described above), wherein the reversion may be carried out be an esterase etc. Other such systems will be well known to those skilled in the art.

The present invention also encompasses pharmaceutical compositions comprising the compounds of the invention. In this regard, and in particular for human therapy, even though the compounds of the present invention (including their pharmaceutically acceptable salts, esters and pharmaceutically acceptable solvates) can be administered alone, they will generally be administered in admixture with a pharmaceutical carrier, excipient or diluent selected with regard to the intended route of administration and standard pharmaceutical practice.

Thus, the present invention also relates to pharmaceutical compositions comprising betulinines or pharmaceutically acceptable salts or esters thereof, together with at least one pharmaceutically acceptable excipient, diluent or carrier.

By way of example, in the pharmaceutical compositions of the present invention, the compounds of the invention may be admixed with any suitable binder(s), lubricant(s), suspending agent(s), coating agent(s), and/or solubilising agent(s). Examples of such suitable excipients for the various different forms of pharmaceutical compositions described herein may be found in the "Handbook of Pharmaceutical Excipients, $2^{nd}$ Edition, (1994), Edited by A Wade and P J Weller.

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

A person of ordinary skill in the art can easily determine an appropriate dose of one of the instant compositions to administer to a subject without undue experimentation. Typically, a physician will determine the actual dosage which will be most suitable for an individual patient and it will vary with the age, weight and response of the particular patient. The dosages disclosed herein are exemplary of the average case. There can of course be individual instances where higher or lower dosage ranges are merited, and such are within the scope of this invention.

In an exemplary embodiment, one or more doses of 10 to 150 mg/day will be administered to the patient for the treatment of malignancy.

The invention further relates to methods of chemical synthesis of the above described compounds.

In one embodiment, the invention relates to a process for preparing compounds of formula I as defined above, comprising:

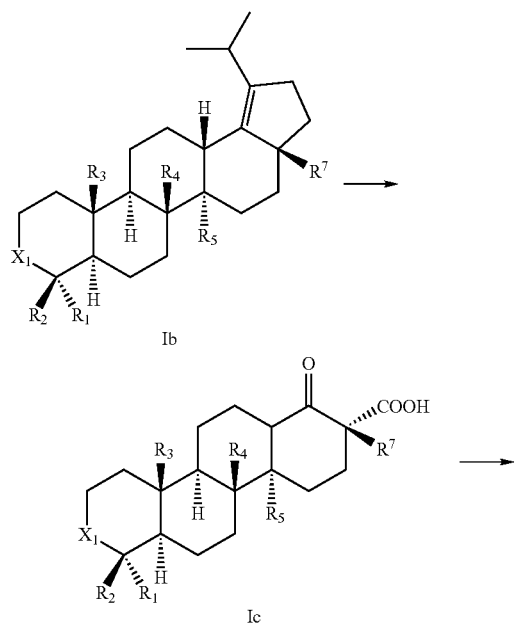

-continued

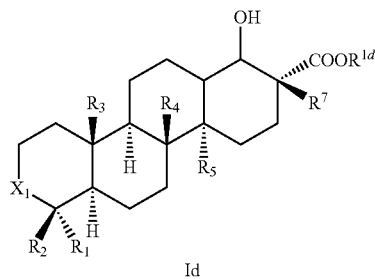

(i) oxidising a compound of formula Ib to a compound of formula Ic;

(ii) reducing said compound of formula Ic to form a compound of formula Id; and optionally (iii) converting said compound of formula Id to a compound of formula I wherein "a" is a double bond.

In a preferred embodiment, the compound of formula Ib is oxidised to Ic by treating sequentially with selenium dioxide, peroxyacetic acid and ruthenium tetroxide.

In a more preferred embodiment, the reduction of Ic to Id is a stereoselective reduction.

Even more preferably, the compound of formula Ic is reduced to Id by treating with sodium borohydride in the presence of a cerium (III) salt In a preferred aspect, step (iii) comprises esterifying a compound of formula Id wherein $R^{1d}$ is H, oxidising and dehydrogenating.

The preparation of the compounds of the present invention will be discussed in greater detail below, with specific reference to the preferred embodiments. The man skilled in the relevant art would be able to prepare other compounds of the invention by selection of the appropriate reagents.

The following scheme illustrates the synthesis of compounds of formula I where $X^1$ is CHOAc, $X^2$ is $CH_2$, $X^3$ is C=O, $R^{1-5}$ are methyl, $R^6$ is H or absent (when "a" is a double bond), $R^7$ is $CH_2OAc$, and $R^8$ is COOH, $COOCH_2OCOMe$, or $COOCH_2OCOC(CH_3)_3$.

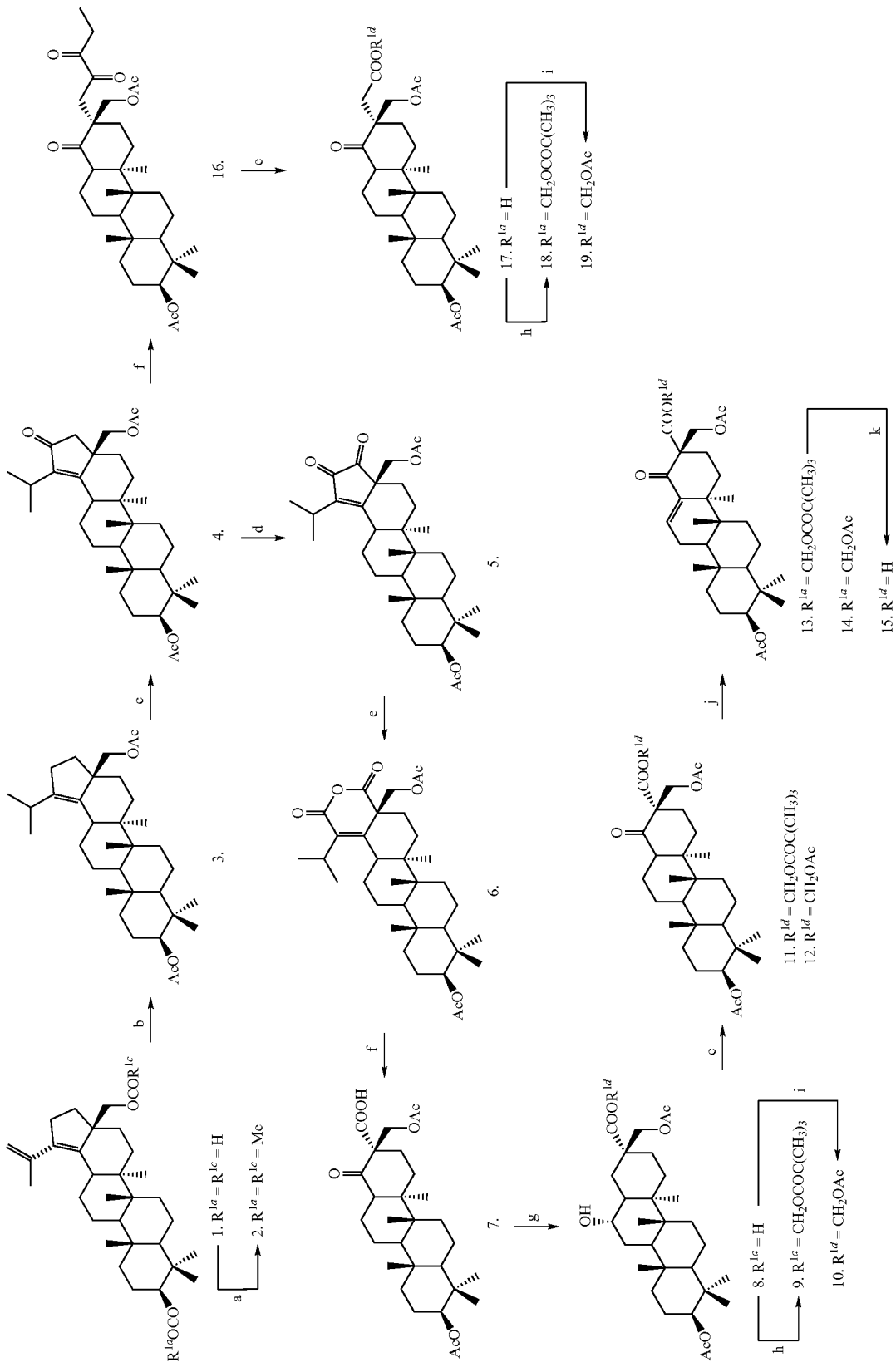

Conditions: a, Acetylation with acetic anhydride in the presence of base (e.g. pyridine); b, isomerisation of double bond by treatment with hydrogen bromide in acetic acid; c, oxidation (e.g. with sodium dichromate); d, oxidation (e.g. with selenium dioxide); e, oxidation (e.g. with peroxyacetic acid); f, fission of double bond (e.g. with ruthenium tetroxide); g, stereoselective reduction (e.g. with sodium borohydride in the presence of a cerium(III) salt); h, esterification with chloromethyl pivalate (POM-Cl) in the presence of base (e.g. 1,8-diazabicyclo[5,4,0]undec-7-ene (DBU)); i esterification with bromomethyl acetate (AcM-Br) in the presence of base (e.g. DBU); j, dehydrogenation (e.g. with selenium dioxide); k, hydrolysis (e.g. with bis(tributyltin)oxide).

The scheme below illustrates the synthesis of compound I.58 of formula I where $X^1$ is CHOAc, $X^3$ is C=O, $R^1$-$R^5$ are methyls, $R^6$ is H, $R^7$ is $CH_2OAc$, $R^8$ is COF.

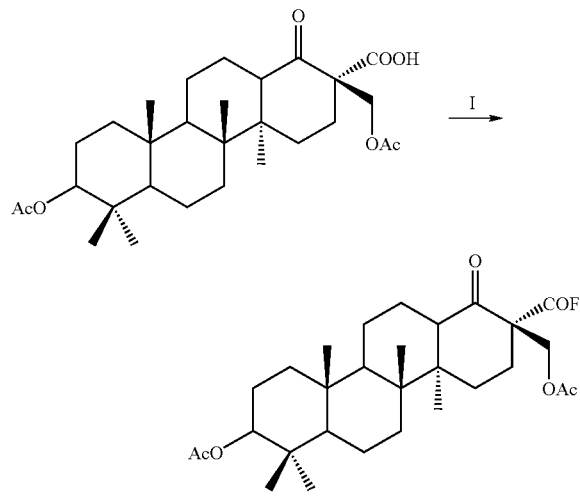

Conditions: 1, reaction with diethylaminosulphur trifluoride.

BRIEF DESCRIPTION OF THE DRAWINGS

The present invention is also described with reference to the accompanying figures wherein.

Figure 1A:
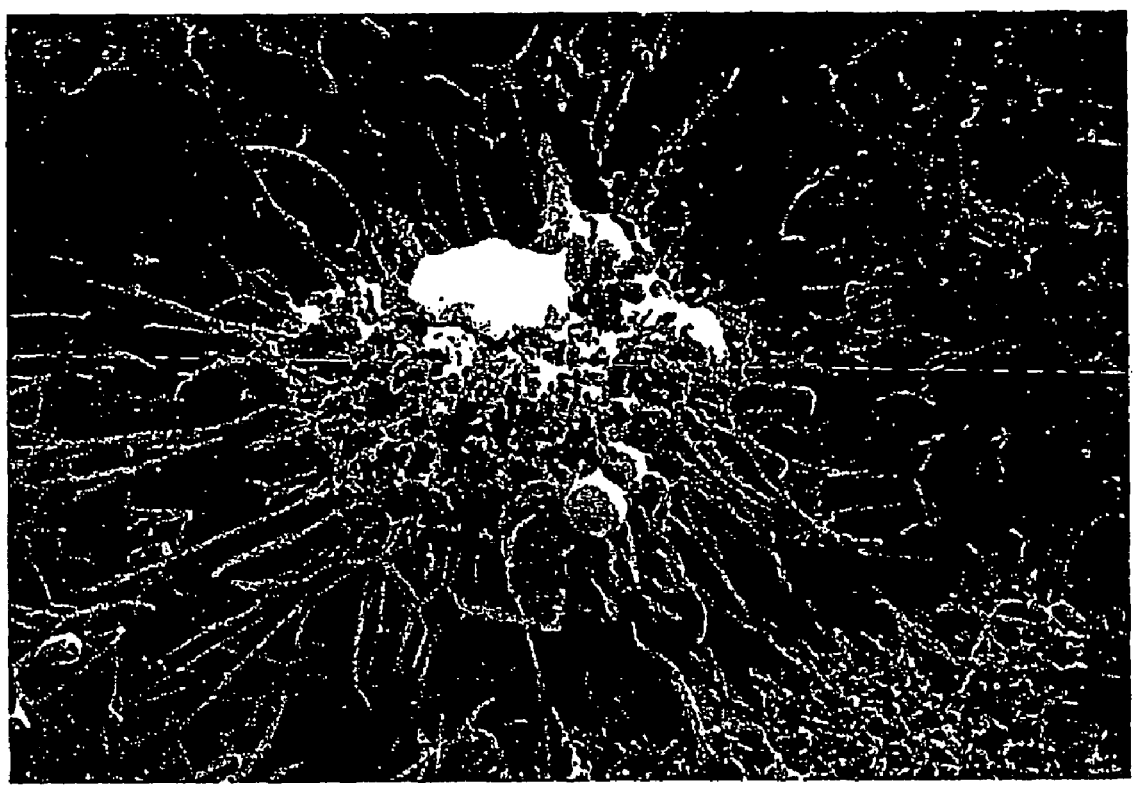
FIG. 1A shows an electron micrograph of a norm, untreated A549 lung cancer cell attached to coverslip with a number of well formed pseudopods and fine structure of cytoplasmatic membrane.
Figure 1B:
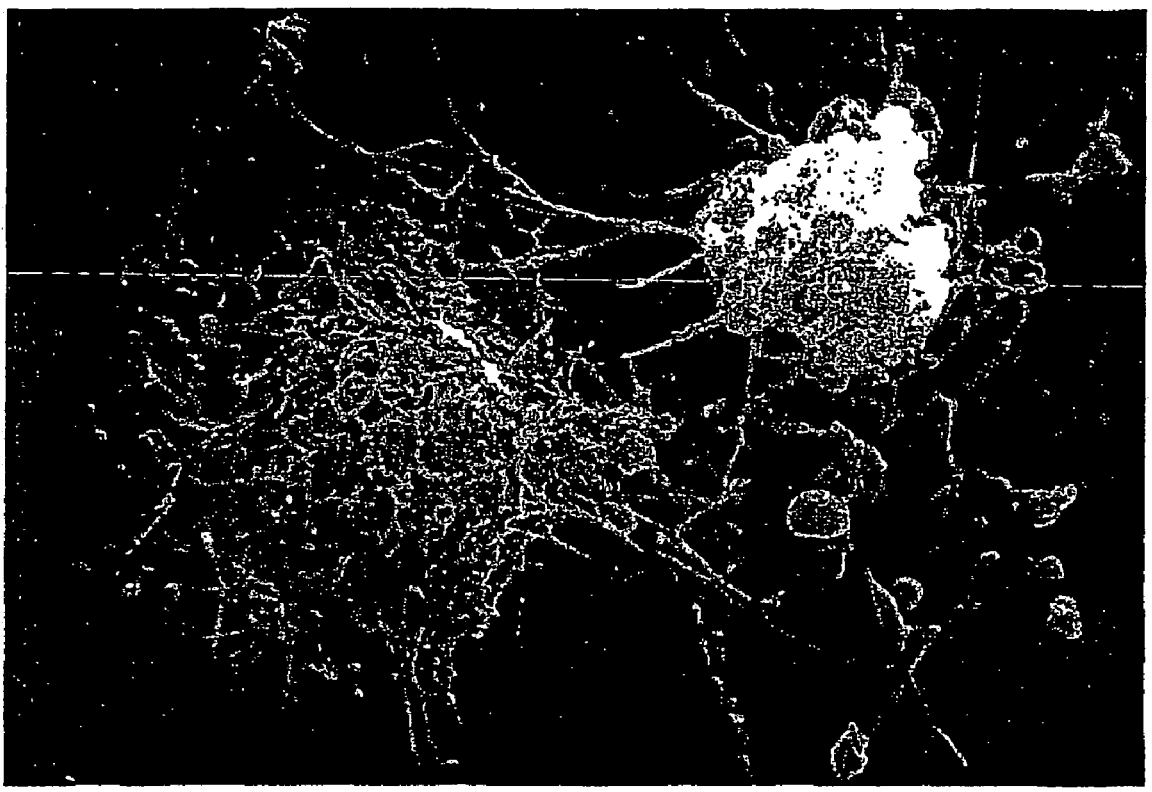
FIG. 1B shows an electron micrograph of betulinic acid treated A549 lung cancer cells. The left cell is attached to the coverslip and exhibits normal morphology with fine cytoplasmatic membrane structure, while the right cell already shows cytoplasmatic membrane blebbing, an early sign of apoptosis.
Figure 1C:
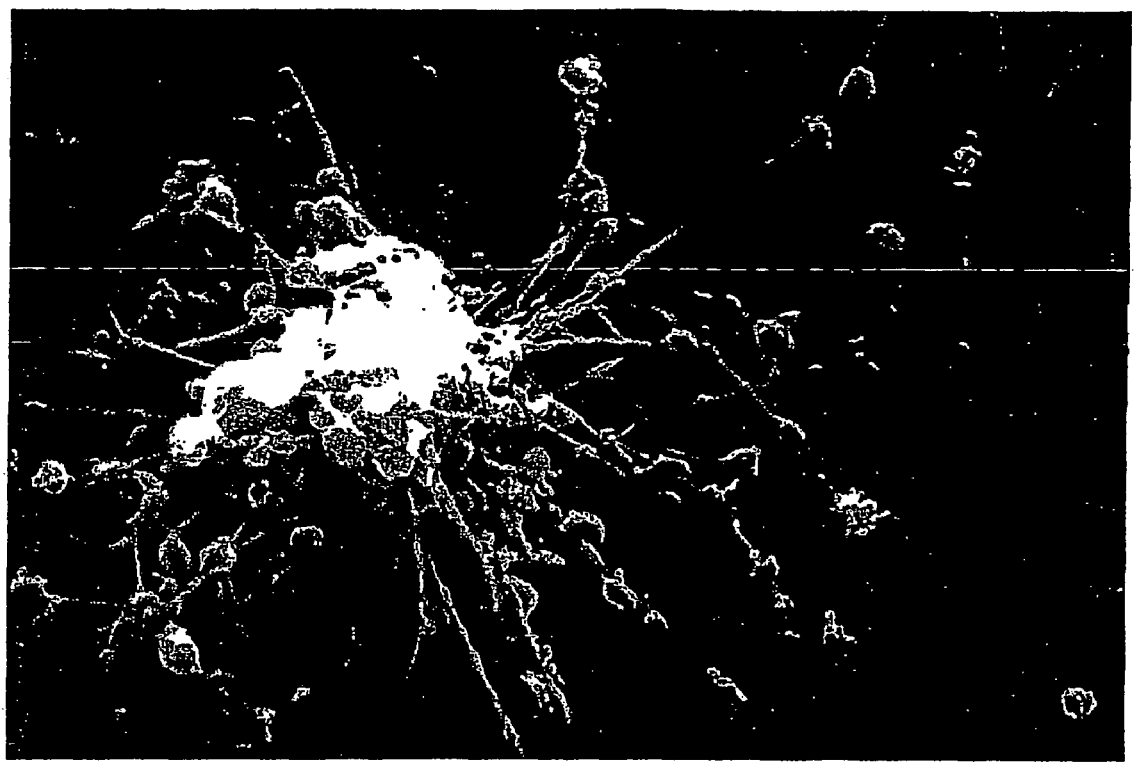
FIG. 1C shows an electron micrograph of I.3 treated A549 lung cancer cells. This illustrates a typical apoptotic tumour cell with extensive cytoplasmatic membrane blebbing, detachment and formation of apoptotic bodies.
Figure 1D:
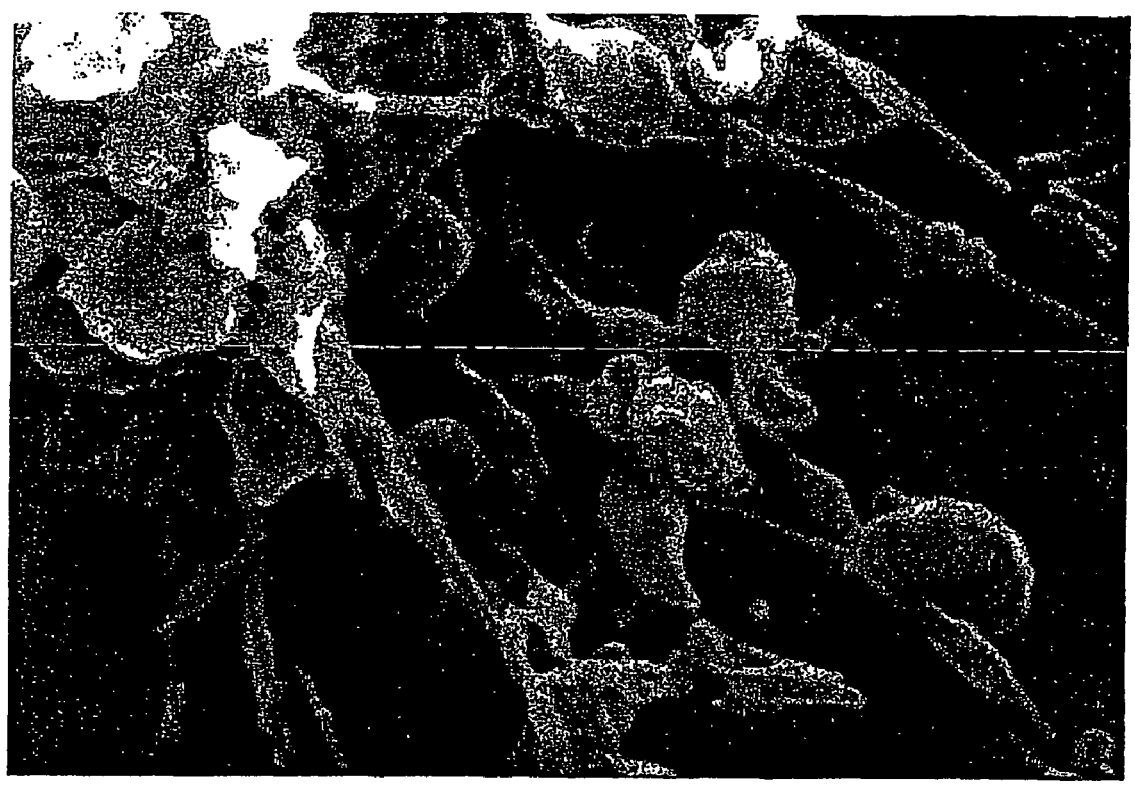
FIG. 1D is a magnification of FIG. 1C, showing details of apoptotic body formation in I.3 treated cells.

More detailed reference to the above figures may be found in the accompanying examples.

This invention is further illustrated by the following examples, which should not be construed as further limiting.

EXAMPLES

General

The chemical shift values (δ-scale, ppm) and coupling constants (J, Hz) in the $^1$H and $^{13}$C NMR spectra were obtained using a Varian UNITY-INOVA 400 FT spectrometer ($^1$H at 400 MHz and $^{13}$C at 100.6 MHz) in deuterochloroform with tetramethylsilane (for $^1$H NMR data δ=0 ppm) as an internal standard. For the $^{13}$C NMR data δ(CDCl$_3$)=77.00 ppm. The value for a multiplet, either defined (doublet (d), triplet (t), quartet (q), septet (sept) or not (m) at the approximate mid point is given unless a range is quoted (s=singlet, b=broad)).

Electron impact mass spectra (EIMS) were measured on an INCOS 50 instrument. Ionising electron energy 75 eV, ion source temperature 150° C. EIMS was used to determine molecular weights, M$^+$ corresponding to the molecular ion.

Ether is diethylether. THF and dioxane were dried over sodium. Acetic acid was purified before use by chromium trioxide treatment and distillation. Reactions were run at room temperature unless otherwise stated. The reaction progress was monitored by thin layer chromatography (TLC) on silicagel 60 G (Merck, detection by spraying with 10% sulphuric acid and heating). The work-up procedure involves dilution with specified solvent (otherwise the organic reaction solvent), exaction with water and then brine or sodium hydrogencarbonate, drying over anhydrous magnesium sulphate, and evaporation under vacuum to give a residue.

Example 1

Lup-20(29)-ene-3β,28-diyl diacetate

Crude betuline (500 g) was dissolved in a mixture of 250 ml pyridine and 250 ml acetic anhydride. The mixture was then refluxed for half an hour. After cooling, the resulting crystals were filtered off and washed with acetic acid, ethanol and water. A solution of crude lup-20(29)-ene-3β,28-diyl diacetate (400 g) in chloroform was filtered through a column of alumina, and the column was washed with chloroform. The filtrate was then evaporated under reduced pressure. The residue was crystallized from chloroform/methanol to obtain 250 g of the title compound which according to TLC contained traces of lupeol acetate. After re-crystallization from chloroform/methanol the yield of pure compound was 239 g, mp. 222-223° C., [α]$_D$+22° (c 0.4; CHCl$_3$). [Schulze H., Pieroh K.: Ber. Dtsch. Chem. Ges. 55, 2332 (1922)].

The $^1$H NMR spectrum of the title compound is as follows:

0.84 s, 0.84 s, 0.85 s, 0.97 s, 1.03 s, 1.68, 6×3H (6×CH$_3$); 2.04 s, 3H, 2.07 s, 3H (2×OAc); 2.44 ddd, 1H (J'=11.4, J''=10.9, J'''=0.7, H-19); 3.85 d, 1H (J=11.1, H-28a); 4.25 dd, 1H, (J'=11.1, J"=1.4, H-28b); 4.47 m, 1H(H-3α); 4.59 m, 1H (ΣJ=3.4, H-29E); 4.69 m, 1H (ΣJ=2.1, H-29Z).

Example 2

Lup-18-ene-3β,28-diyl diacetate

A solution of hydrogen bromide in acetic acid (38%, 1.4 l) was added to a solution of lup-20(29)-ene-3β,28-diyl diacetate (100 g, 190 mmol) in a mixture of benzene, acetic acid and acetic anhydride (1 l:0.5 l:50 ml). The reaction mixture was refluxed until the reaction was completed (TLC was developed in hexane/ether mixture). After cooling, the reaction mixture was poured into ice cold water (3:1) and extracted with benzene (3×0.5 l). The combined organic phases were washed with NaHCO₃ aqueous solution, NaHSO₃ solution and water and dried over magnesium sulphate. Usual working up procedure gave 90 g of dark brown residue. The dry powder was extracted in a Soxhlet extractor with acetone until it turned white. After drying in the air, the product was crystallized from butanone. The yield of the title compound was 74 g (74%), mp. 215-216° C., $[\alpha]_D$+15° (c 0.45; CHCl₃). [Suokas E., Hase T.: Acta Chem. Scand., B 29, 139 (1975)].

The $^1$H NMR spectrum of the title compound is as follows: 0.84 s, 0.85 s, 0.89 s, 0.90 s, 0.91 d, 3H (J=6.8), 0.99 d, 3H (J=6.8), 1.06 s, 7×3H (7×CH₃); 2.04 s, 3H, 2.05 s, 3H (2×OAc); 2.25 m, 2H (ΣJ~15); 2.43 m, 1H (ΣJ~15); 3.14 sept, 1H (J=7, H-20); 3.98 d, 1H (J=10.8, H-28a); 4.03 d, 1H (J=10.8, H-28b); 4.49 m, 1H(H-3α).

Example 3

21-oxo-lup-18-ene-3β,28 diyl diacetate

Lup-18-ene-3β,28-diyl diacetate (50 g; 95 mmol), sodium dichromate (22.5 g; 75.5 mmol) and sodium acetate (5 g) were dissolved in a mixture of benzene and acetic acid (0.7 l, 0.3 l). The reaction mixture was allowed to stand until the reaction was completed (TLC was developed in hexane/ether). After dilution with an excess of water, the mixture was extracted with benzene (3×300 ml). After usual working up procedure the title compound was obtained (45 g, 87%) as a pale-yellow crystalline foam which was used in the next step without further purification (see Example 4). Pure title compound has m.p. 205-206° C., $[\alpha]_D$−35° (c 0.49; CHCl₃). Another way to the title compound is described in Sejbal J., Klinot J., Budešínský M., Protiva J.: Collect. Czech. Chem. Commun. 56, 2936 (1991).

The $^1$H NMR spectrum of the title compound is as follows: 0.85 s, 0.86 s, 0.93 s, 0.94 s, 1.16 s, 1.17 d (J=7.1), 1.21 d (J=7.1), 7×3H (7×CH₃); 2.00 s, 3H, 2.05 s, 3H (2×OAc); 2.39 d, 1H (J=18.5, H-22); 2.87 dd, 1H(J'=11.9, J"=4.1, H-13β); 3.18 sept, 1H (J=6:6, H-20); 4.06 d, 1H (J=10.9, H-28a); 4.34 d, 1H (J=10.9, H-28b); 4.49 m, 1H (J~7, H-3α).

The following compounds were prepared by the above-mentioned procedure:
(pivaloyloxy)methyl 3β,28-diacetoxy-18-oxo-19,20,21,29,30-pentanorlupan-22-oate
acetoxymethyl 3β,28-diacetoxy-18-oxo-19,20,21,29,30-pentanorlupan-22-oate

Example 4

21,22-dioxolup-18-ene-3β,28-diyl diacetate

A solution of crude 21-oxolup-18-ene-3β,28-diyl diacetate (40g; 74 mmol; containing about 85% of 21-oxo-lup-18-ene-3β,28-diyl diacetate) and selenium dioxide (160 g; 1.44 mol) in a mixture of dioxane (0.8 l) and acetic acid (0.4 l) was refluxed until the reaction was completed (TLC was developed in benzene/ether).

After cooling, the precipitated selenium was removed by filtration and the filtrate was slowly poured into a vigorously stirred excess of water. The red-orange precipitate was filtered off under reduced pressure, carefully washed with water and dried in the air. Dry crude 21,22-dioxo-lup-18-ene-3β,28-diyl diacetate was dissolved in chloroform and the solution was filtered through a column of alumina, the column was then washed with chloroform, and the filtrate was evaporated under reduced pressure. The residue was crystallized from methyl acetate to give 28.9 g (82%) of the title compound as pale-orange needles, mp. 267-270° C., $[\alpha]_D$−127° (c 0.32; CHCl₃). Another way to the title compound is described in Klinotová E., Cermáková J., Rejzek M., Krecek V., Sejbal J., Olšovský P., Klinot J.: Collet. Czech. Chem. Commun. 64, 329 (1999).

The $^1$H NMR spectrum of the title compound is as follows: 0.85 s, 0.86 s, 0.94 s, 0.97 s, 1.18 s, 1.24 d (J=7.2), 1.26 d (J=7.2), 7×3H (7×CH₃); 1.93 s, 3H, 2.06 s, 3H (2×OAc); 3.12 dd, 1H (J'-12.5, J"=3.8, H-13β); 3.36 sept, 1H (J=7.0, H-20); 4.02 d, 1H (J=11.1, H-28a); 4.49 dd, 1H (=10.2, J"=6.0, H-3α); 4.84 d, 1H (J=11.1, H-28b).

The following compounds were prepared by the above-mentioned procedure:
methyl 3β-acetoxy-21,22-dioxolup-18-en-28-oate
acetoxymethyl 3β-acetoxy-21,22-dioxolup-18-en-28-oate
(pivaloyloxy)methyl 3β-acetoxy-21,22-dioxolup-18-en-28-oate
acetoxymethyl 30,28 diacetoxy-18-oxo-19,20,21,29,30-pentanorlup-12-en-22-oate
(pivaloyloxy)methyl 3β,28-diacetoxy-18-oxo-19,20,21,29,30-pentanorlup-12-en-22-oate
3β-hydroxy-30-oxolup-20(29)-en-28-oic acid [Dinda B., Hajra A. K., Das S. K., Chel G., Chakraborty R., Ranu B. C.: Indian. J. Chem., Sect. B 34, 624 (1995)].
acetoxymethyl 3β-hydroxy-30-oxolup-20(29)-en-28-oate
(pivaloyloxy)methyl 3β-hydroxy-30-oxolup-20(29)-en-28-oate

Example 5

Anhydride of 3β,28-diacetoxy-21,22-secolup-18-ene-21,22-dioic acid

A solution of 21,22-dioxolup-18-ene-3β,28-diyl diacetate (25 g; 45 mmol) and peroxyacetic acid (0.6 l; 32%) in chloroform (0.25 l) was vigorously stirred until the reaction was completed (TLC was developed in hexane/ether). The colourless reaction mixture was diluted with cold water and extracted with chloroform (3×200 ml). The combined organic phases were washed with 5% aqueous solution of potassium iodide (400 ml), saturated aqueous solution of sodium sulphite (200 ml) and brine (2×200 ml), dried and evaporated. The resulting pale-yellow oil was crystallized from chloroform/methanol to give 20.7 g (80.5%) of the title compound as small white crystals, m.p. 306-309° C., $[\alpha]_D$+88° (c 0.45; CHCl₃). Another way to the title compound is described in Sejbal J., Klinot J., Budešínský M., Protiva J.: Collect. Czech. Chem. Commun. 56, 2936 (1991).

The $^1$H NMR spectrum of the title compound is as follows: 0.85 s, 0.85 s, 0.90 s, 0.91 s, 1.11 s, 1.14 d (=7), 1.31 d (J=7), 7×3H (7×CH₃); 2.01 s, 3H, 2.05 s, 3H (2×OAc); 2.53 dt, 1H (J'=14.4, J"=J'"=3.5); 2.72 dd, 1H (J'=3.1, J'-12.3); 3.26 sept., 1H(H-20, J=7); 3.90 d, 1H, 4.54 d, 1H (2×H-28, J=11.0); 4.47 m, 1H(H-3α).

The following compounds were prepared by the above-mentioned procedure:
3β,28-diacetoxy-18-oxo-18,19-seco-19,20,29,30-tetranor-lupan-21-oic acid [Sarek J., Klinot J., Klinotová E., Sejbal J.: Chem. Listy 91, 1005 (1997)],
3β,28-diacetoxy-18-oxo-19,20,21,29,30-pentanorlupan-22-oic acid.

Example 6

3β,28-diacetoxy-18-oxo-19,20,21,29,30-pentanorlupan-22-oic acid

The anhydride of 3β,28 acetoxy-21,22-secolup-18-ene-21,22-dioic acid (20 g; 35.1 mmol) in ethyl acetate (1 l) was added to a mixture of ruthenium dioxide (400 mg; 4 mmol), sodium metaperiodate (60 g, 280.3 mmol), water (200 ml) and trifluoroacetic acid (20 ml), and the mixture was vigorously stirred. After the reaction was completed, ethanol was added, the mixture was filtered, and the organic layer was filtered through a short silica gel column. The column was then washed with ethyl acetate, the filtrate was evaporated under the reduced pressure and residue was washed with ether and crystallized from a mixture of dichloromethane/ether. The yield of the title compound was 10.6 g (61%), m.p. 137-140° C., $[\alpha]_D$+40° (c 0.37; CHCl$_3$). [Sarek J., Klinot J., Klinotová E., Sejbal J.: Chem. Listy 91, 1005 (1997)].

The $^{13}$C NMR spectrum of the title compound is as follows:
213.3, 174.2, 171.1, 170.5, 80.7, 65.4, 58.8, 55.4, 50.6, 50.1, 46.8, 41.1, 38.5, 37.8, 37.1, 33.9, 28.4, 27.9, 26.8, 23.5, 21.8, 21.2, 20.6, 19.6, 18.1, 16.7, 16.5, 16.2, 16.0.

The following compounds were prepared by the above-mentioned procedure:
18,19,21-trioxo-18,19-secolupane-3β,28-diyl diacetate [Sarek J., Klinot J., Klinotová E., Sejbal J.: Chem. Listy 91, 1005 (1997)].
18,19,21,22-tetraoxo-18,19-secolupane-3β,28-diyl diacetate
3β-acetoxy-21-oxolup-18-en-28-oic acid

Example 7

3β,28-diacetoxy-18-hydroxy-19,20,21,29,30-pentanorlupan-22-oic acid

To a solution of 3β,28-diacetoxy-18-oxo-19,20,21,29,30-pentanorlupane-22-oic acid (10 g; 19.8 mmol) in 500 ml THF, a solution of cerium chloride (200 ml; 1 M) and sodium borohydride (2 g; 53 mmol) was added. The reaction mixture was stirred for one hour. The mixture was poured into an excess of 1% aqueous solution of hydrochloric acid and extracted with chloroform (3×300 ml). The usual working up procedure gave 8.7 g (86.7%) of title compound, m.p. 156-159° C., $[\alpha]_D$+48° (c 0.32; CHCl$_3$).

The $^{13}$C NMR spectrum of the title compound is as follows: 179.5, 171.1, 170.9, 80.9, 73.5, 64.5, 55.4, 51.7, 50.6, 41.0, 40.3, 38.4, 37.8, 37.3, 37.1, 32.6, 27.9, 25.9 (2 C), 23.6, 21.3, 20.9, 20.8, 19.9, 18.0, 16.5, 16.3, 16.1, 16.0.

Example 8

(pivaloyloxy)methyl-3β,28-diacetoxy-18-hydroxy-19,20,21,29,30-pentanorlupan-22-oate DBU (0.3 g; 2 mmol) and chloromethylpivalate (0.3 g; 2 mmol) were added to the solution of 3β,28-diacetoxy-18-hydroxy-19,20,21,29,30-pentanorlupan-22-oic acid (1 g; 2 mmol) in a mixture of dichloromethane (5 ml) and acetonitrile (2 ml). The mixture was vigorously stirred for 3 hours and then diluted with an ice-cold water and extracted with chloroform (3×, 10 ml). Collected organic extracts were washed with cold brine, dried and chloroform was evaporated in vacuum. The resulting viscous pale yellow oil (1.5 g) was chromatographed on silicagel, eluting with toluene. After the crystallization from methanol, 0.6 g (48%) of the title compound was obtained in the form of colorless needles, m.p. 235-240° C., $[\alpha]_D$+53° (c 0.23; CHCl$_3$).

The $^{13}$C NMR spectrum obtained for the title compound is as follows: 177.4, 172.9, 171.0, 170.6, 80.8, 80.0, 73.5, 64.1, 55.4, 52.1, 50.6, 41.0, 40.3, 38.8, 38.5, 37.8, 37.3, 37.1, 32.7, 27.9, 26.8 (3 C), 25.9, 25.8, 23.6, 21.3, 20.9, 20.7, 19.8, 18.1, 16.5, 16.3, 16.1, 16.0.

The following esters were prepared via this general procedure:
(pivaloyloxy)methyl-3β,28-diacetoxy-18-oxo-18,19-seco-19,20,29,30-tetranorlupan-21-oate
(pivaloyloxy)methyl-3β-hydroxy-30-oxo-lup-20(29)-en-28-oate
(pivaloyloxy)methyl-3β-acetoxy-21-oxo-lup-18-en-28-oate In the same manner, using AcM-Br instead of POM-Cl, following esters were prepared.
Acetoxymethyl-3β,28-diacetoxy-18-hydroxy-19,20,21,29,30-pentanorlupan-22-oate
Acetoxymethyl-3β,28-diacetoxy-18-oxo-18,19-seco-19,20,29,30-tetranorlupan-21-oate
Acetoxymethyl-3β-hydroxy-30-oxolup-20(29)-en-28-oate
Acetoxymethyl-3β-acetoxy-21-oxolup 18-en-28-oate

Example 9

3β,28-diacetoxy-18-oxo-19,20,21,29,30-pentanor-lup-12-en-22-oic acid

Bis(tributyltin)oxide (1.9 g; 3.2 mmol) was added to a solution of (pivaloyloxy)methyl 3β,28-diacetoxy-18-oxo-9,20,21,29,30-pentanorlup-12-en-22-oate (1 g; 1.6 mmol) and AIBN (20 mg) in ether (50 ml). The mixture was vigorously stirred until the reaction was completed (TLC was developed with chloroform/ethyl acetate).

Ether was then evaporated under vacuum and the product was purified by chromatography on silicagel, eluting with chloroform/ethyl acetate. After crystallization from a dichloromethane/ether mixture the title compound was obtained in the form of white crystalline solid (0.5 g, 62%), m.p. 138-141° C., $[\alpha]_D$+38° (c 0.25; CHCl$_3$).

The $^{13}$C NMR spectrum is as follows: 16.0, 16.7, 16.9, 18.1, 20.8, 21.3, 23.4, 24.2, 24.4, 24.6, 25.2, 27.8, 33.4, 36.8, 37.7, 38.3, 38.7, 43.9, 46.9, 55.4, 58.9, 64.3, 80.5, 138.1, 140.6, 170.5, 170.9, 171.6, 196.8.

Example 10

3β,28-diacetoxy-18-oxo-19,20,21,29,30-pentanor-lup-22-oyl fluoride and similar compounds Diethylaminosulphur trifluoride (0.5 ml; 3.25 mmol) was added dropwise to a solution of 3β,28-diacetoxy-18-oxo-19,20,21,29,30-pentanorlup-22-oic acid (0.5 g; 1.0 mmol) in dry chloroform (5 ml) and the reaction mixture was stirred overnight at room temperature. After the reaction was complete, the mixture was slowly poured into cold water (50 ml) and extracted twice with chloroform. The combined organic fractions were worked up in the general manner and chromatographed on silica gel (20% ethyl acetate in hexane). The residue was crystallized from isopropyl alcohol to give 0.19 g (38%) of the title compound as white crystals, m.p. 150-155° C. (decomp.), $[\alpha]_D+21°$ (c 0.55; CHCl$_3$).

The $^{13}$C NMR spectrum of the title compound is as follows: 211.3 s, 160.2 d (J=374), 170.1 s, 169.5 s, 80.6 s, 65.4 s, 57.5 d (J=39), 55.1 s, 50.6 s, 49.9 s, 46.8 s, 40.1 s, 38.5 s, 37.8 s, 36.1 s, 33.3 s, 28.4 s, 27.9 s, 26.8 s, 23.5 s, 21.3 s, 21.2 s, 20.6 s, 19.6 s, 18.0 s, 16.5 s, 16.4 s, 16.2 s, 15.9 s.

Example: 11

Biological Activity of Betulinines 11.1. In Vitro Cytotoxic Activity of Betulinines on Tumor Cell Lines One of the parameters used as the basis for colorimetric assays is the metabolic activity of viable cells. For example, a microtiter assay which uses the tetrazolium salt MTT is now widely used to quantitate cell proliferation and cytotoxicity [Hajdúch M, Mihál V, Minarík J, Fáber E, Safárová M, Weigl E, Antálek P.: Cytotechnology, 1996, 19, 243-245]. For instance, this assay is used in drug screening programs and in chemosensitivity testing. Because tetrazolium salts are cleaved only by metabolically active cells, these assays exclusively detect viable cells. In the case of the MTT assay, yellow soluble tetrazolium salt is reduced to a coloured water-insoluble formazan salt. After it is solubilized, the formazan formed can easily and rapidly be quantified in a conventional ELISA plate reader at 570 nm (maximum absorbancy). The quantity of reduced formazan corresponds to the number of vital cells in the culture.

Human T-lymphoblastic leukaemia cell line CEM was used for routine screening of these compounds. To prove a common mechanism of action, selected compounds which showed activity in a screening assay were tested in a panel of cell lines (Table 2). These lines were from different species and of different histogenetic origin and they possess various alterations in cell cycle regulatory proteins and hormone dependence status (Table 2). The cells were maintained in Nunc/Corning 80 cm$^2$ plastic tissue culture flasks and cultured in cell culture medium (DMEM with 5 g/l glucose, 2 mM glutamine, 100 U/ml penicillin, 100 µg/ml streptomycin, 10% foetal calf serum and sodium bicarbonate). Individual compounds were dissolved in 10% dimethylsulfoxide/saline, pH 8.0.

The cell suspensions that were prepared and diluted according to the particular cell type and the expected target cell density (2.500-30.000 cells per well based on cell growth characteristics) were added by pipette (80 µl) into 96/well microtiter plates. Inoculates were allowed a pre-incubation period of 24 hours at 37° C. and 5% CO$_2$ for stabilisation. Four-fold dilutions of the intended test concentration were added at time zero in 20 µl aliquots to the microtiter plate wells. Usually, test compounds were evaluated at six 4-fold dilutions. In routine testing, the highest well concentration was 250 µM, but it may differ, depending on the agent. All drug concentrations were examined in duplicate. Incubations of cells with the test compounds lasted for 72 hours at 37° C., in 5% CO$_2$ atmosphere and 100% humidity. At the end of the incubation period, the cells were assayed by using the MIT assay. Ten microliters of the MTT stock solution were pipetted into each well and incubated further for 1-4 hours. After this incubation period, formazan was solubilized by the addition of 100 µd/well of 10% SDS in water (pH=5.5) followed by further incubation at 37° C. overnight. The optical density (OD) was measured at 540 nm with the Labsystem iEMS Reader MF(UK). The tumour cell survival (TCS) was calculated using the following equitation: TCS=(OD$_{drug\ exposed\ well}$/mean OD$_{control\ wells}$)×100%. The TCS$_{50}$ value, the drug concentration lethal to 50% of the tumour cells, was calculated from the obtained dose response curves.

To evaluate the anti cancer activity of betulinines, their cytotoxic activity against CEM cell line was examined using the screening assay. Potent compounds were further tested against a panel of cell lines of different histogenetic and species origin (Table 2).

TABLE 2

Cytotoxic activity of selected betulinines against a panel of different (non)malignant cell lines.

| Cell Line | Description | Compound (TCS$_{50}$[µM]) | | | | | | |
|---|---|---|---|---|---|---|---|---|
| | | Betulinic acid | I.3 | I.7 | I.28 | I.44 | I.55 | I.57 |
| B16 | mouse melanoma | 36 | 2.1 | | | | | |
| B16F | mouse melanoma, metastatic | 4.6 | 4.7 | | | | | |
| SW620 | human colon cancer, metastasis | 250 | 1.2 | | | | | |
| U87MG | human glioblastoma | 250 | 5.1 | | | | | |
| HepG2 | human hepatocellular carcinoma | 3.6 | 1.7 | | | | | |
| A549 | human lung adenocarcinoma | 236 | 1.0 | | | | | |
| MCF-7 | human breast cancer, estrogen dependent, p53+/+, Rb+/+ | 194 | 2.3 | | | | | |
| U2OS | human osteosarcoma, p53+/−, Rb+/− | 250 | 1.5 | | | | | |
| Saos2 | human rhabdomyosarcoma, p53−/−, Rb−/− | 250 | 1.8 | | | | | |
| BT549 | human breast cancer, p53mut/mut | 250 | 2.0 | | | | | |
| MDA-MB-238 | human breast cancer, estrogen independent, p53mut/mut | 195 | 1.4 | | | | | |
| DU145 | human prostate cancer, androgen independent, Rb−/− | 241 | 0.8 | | | | | |

TABLE 2-continued

Cytotoxic activity of selected betulinines against a panel of different (non)malignant cell lines.

| Cell Line | Description | Betulinic acid | I.3 | I.7 | I.28 | I.44 | I.55 | I.57 |
|---|---|---|---|---|---|---|---|---|
| HT-29 | human colon cancer | 250 | 1.6 | | | | | |
| OVCAR-3 | human ovarian cancer | 164 | 1.0 | | | | | |
| Caco-2 | human colon cancer | 20 | 3.0 | | | | | |
| MEL-3 | human melanoma | 2.7 | 1.3 | | | | | |
| Lymphocytes | human normal lymphocytes | 250 | 13 | | | | | |
| NIH3T3 | mouse immortalised fibroblasts | 250 | 7.2 | | | | | |
| K562 | human promyelocytic leukemia | 250 | 0.2 | | | | | |
| K562-CdA | human promyelocytic leukemia, cladrubin resistant | 250 | 0.3 | | | | | |
| K562-GEM | human promyelocytic leukemia, gemcitabin resistant | 101 | 0.9 | | | | | |
| K562-ARA-C | human promyelocytic leukemia, cytarabin resistant | 250 | 0.6 | | | | | |
| K562-FLUD | human promyelocytic leukemia, fludarabin resistant | 250 | 0.4 | | | | | |
| CEM | human T-lymphoblastic leukemia | 250 | 1.0 | 5.0 | 18 | 11 | 26 | 0.2 |
| CEM-DNR 1/C2 | human T-lymphoblastic leukemia, daunorubicin resistant | 250 | 0.6 | | | | | |
| CEM-DNR bulk | human T-lymphoblastic leukemia, daunorubicin resistant | 250 | 1.1 | | | | | |
| CEM-VCR 1/F3 | human T-lymphoblastic leukemia, vincristin resistant | 19 | 3.3 | | | | | |
| CEM-VCR 3/D5 | human T-lymphoblastic leukemia, vincristin resistant | 24 | 2.9 | | | | | |
| CEM-VCR bulk | human T-lymphoblastic leukemia, vincristin resistant | 69 | 2.5 | | | | | |

In contrast to betulinic acid, which is reported to be an agent selective for neuroectodermal derived tumours, there was no significant difference in sensitivity of betulinines to tumours of different histogenetic origin The compounds are effective in submicromolar or low micromolar concentrations. However, the non-malignant cells, e.g. NIH3T3 fibroblasts and normal human lymphocytes, tolerated substantially higher doses of betulinines than the tumour cells suggesting a favourable therapeutic index.

Notably, the effectiveness of betulinines was found to be identical in cell lines bearing various mutations or deletions in cell cycle associated proteins Table 2). This indicates that these substances should be equally effective in tumours with various alterations of tumour suppresser genes, namely p53, Rb, etc.

Furthermore, betulinines were shown to be equally effective in drug resistant cell lines as on their maternal counterparts, thereby suggesting that classical mechanisms of multidrug resistance apparently do not apply to these compounds. This particular characteristic should be of significant therapeutic benefit to chemotherapy resistant cancer patients.

Finally, the cytotoxic activity of betulinines is independent of the hormonal status of cancer cells, so the compounds should be equally effective in treatment of hormone dependent and independent cancers.

11.2. Betulinines Induce Apoptosis in Tumour Cells.

To analyse the mechanisms of betulinine-induced cytotoxicity, it is important to distinguish apoptosis from the other major form of cell death, necrosis. Firstly, at the tissue level, apoptosis produces little or no inflammation, since shrunken portions of the cell are engulfed by the neighbouring cells, especially macrophages, rather than being released into the extracellular fluid. In contrast, in necrosis, cellular contents are released into the extracellular fluid, and thus have an irritant affect on the nearby cells, causing inflammation. Secondly, at the cellular level, apoptotic cells exhibit shrinkage and blebbing of the cytoplasm, preservation of structure of cellular organelles including the mitochondria, condensation and margination of chromatin, fragmentation of nuclei and formation of apoptotic bodies, thought not all of these are seen in all cell types. Thirdly, at the molecular level, a number of biochemical processes play an important role in the induction of apoptosis. However, the majority of them are not well understood, and they result in activation of proteases and nucleases, which finally distruct key biological macromolecules—proteins and DNA. For the detection of apoptotic versus necrotic modes of cell death, the morphology was assessed by scanning electron microscopy.

A549 cell line was cultured on tissue culture treated glass coverslips in 6-well culture plates with or without 2 µM concentration of I.3 or betulinic acid at 37° C. and 5% $CO_2$ for 12 hours. Following incubation, the coverslips were washed in Hank's buffered salt solution and processed as described below.

Cells were fixed in 2% glutaldehyde/PBS overnight at 4° C., dried and covered with gold under vacuum. The surface of the cells was examined for typical morphologic markers of apoptosis under a scanning electron microscope (Tesla, Czech Republic).

Initial phase contrast microscopy examination indicated that betulinines induce typical morphological features of apoptosis in cancer cells. This was later confirmed by electron microscopy (FIG. 1). Typical morphological criteria of apoptosis were identified in cells treated with betulinine I.3: cytoplasmatic blebbing, cellular fragmentation and formation of apoptotic bodies.

11.3. In Vivo Activity of Betulinine I.3.

Animal tumour systems are important models for determining the ability of a compound to be adsorbed into the blood stream, to penetrate into the tumour compartment and to kill factions of proliferating or resting tumour cells at minimally toxic doses. Although subject to criticism, in vitro/in vivo models have identified all of the chemotherapeutic agents effective in current clinical practice. It is well recognised that most compounds are efficacious in lymphomas and leukemias, whereas few have proved to be effective in solid tumours, illustrating that there are major differences between animal models and clinical situations. Solid tumours of different histogenetic origin are implanted subcutaneously or intramuscularly into animals which are then treated with a single agent. Inhibition of solid tumour growth is thus a parameter related to the activity of the drug. Conversely, in patients primary tumours are controlled by surgery and radiation, together with polychemotherapy. Usually, the acceptable criterion for activity is >50% tumour regression. However, drugs active in several different screening systems are more likely to be effective in humans; for instance, doxorubicin, cyclophosphamide and cisplatin have a broad spectrum of activity in animal tumour models. Moreover, with regard to toxicity and total drug exposure, a correlation has been found between mice and man for most active antitumor drugs.

Betulinic acid was reported to exhibit prominent activity in neuroectodermal tumours, e.g. melanoma, primitive neuroectodermal tumours (PNET) and neuroblastoma. The latter is the most lethal solid tumour of childhood as it is considered to be one of the most drug resistant tumours. In the light of this knowledge, the activity of I.3 in xenotransplanted human neuroblastoma was of particular interest, although this compound demonstrated broad anti-cancer activity under in vitro conditions.

Human neuroblastoma SK-N-AS cell line was obtained from ATTC. The line was cultured in Dulbeco's modified essential medium with 4.5 g dextrose/l, 10% of foetal calf serum, 2 mM glutamine, 100 U/ml penicillin and 100 mg/ml streptomycin. For transplantation purposes, only the cells in log phase were used.

CD-1/Ctrl-1 nu/nu nude female mice, 8 weeks old, 18-22 g weight were used in this study (IffaCredo, France). Animals were inoculated with $5.10^6$ tumour cells subcutaneously into right inquinal region. Following transplantation, tumor growth was measured in both the control/vehicle and the treated groups using calipers. Tumor volume (TV) was calculated as follows: $TV=(a^2 \times b)2$, where a is width and b is length. The statistical significance was evaluated using a nonparametric t-test.

Cisplatin (Platidiam 10 inj, sicc., Lachema, Czech Republic) was used as a control drug in this experiment. It was diluted in apyrogenic water and applied to animals in a final volume of 0.18 ml subcutaneously at day 1.

I.3 was synthesised as described above. It was suspended at 10 mg(ml in 5% dextrose and pH was adjusted to 8.0 with sodium hydroxide.

vehicle: 5% dextrose with pH adjusted to 8.0 with sodium hydroxide.

Figure 2:
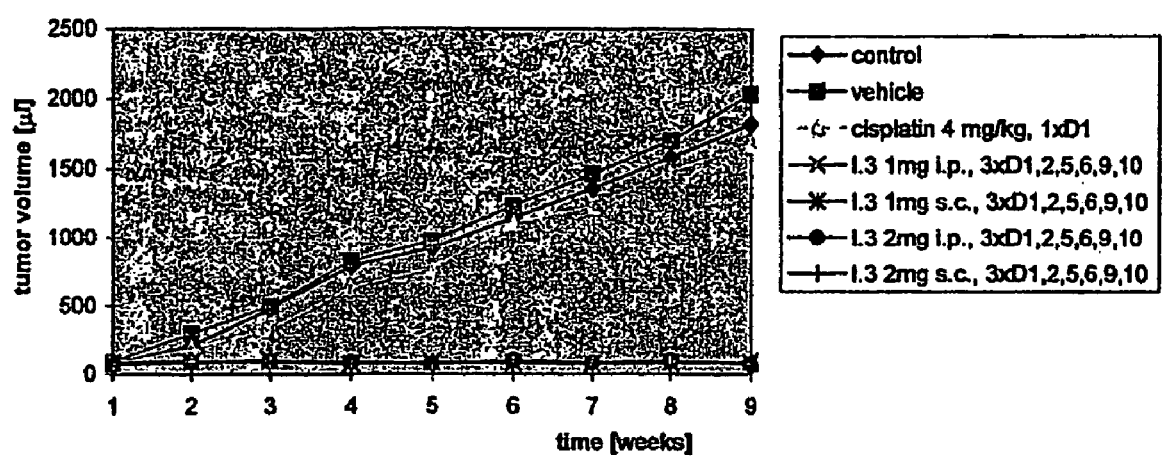
FIG. 2 shows the anticancer activity of betulinine I.3 in xenotransplantated human SK-N-AS neuroblastoma.

Animals were treated with drugs/vehicle 24 hours after transplantation. The following groups (with 10 animals per group) were created:
control—untreated animals
vehicle—0.2 ml of vehicle applied to animals at 3×D1, 2, 5, 6, 9, 10 intraperitoneally
cisplatin 4 mg/kg—0.18 ml of cisplatin solution applied to animals subcutaneously at 1×D1
I.3 1 mg/mouse s.c.—0.1 ml of I.3 suspension applied to animals at 3×D1, 2, 5, 6, 9, 10 subcutaneously
I.3 2 mg/mouse s.c.—0.2 ml of I.3 suspension applied to animals at 3×D1, 2, 5, 6, 9, 10 subcutaneously
I.3 1 mg/mouse i.p.—0.1 ml of I.3 suspension applied to animals at 3×D1, 2, 5, 6, 9, 10 intraperitoneally
I.3 2 mg/mouse i.p.—0.2 ml of I.3 suspension applied to animals at 3×D1, 2, 5, 6, 9, 10 intraperitoneally The results of the study are summarised in FIG. 2. The anticancer activity of I.3 is clearly demonstrated, since there is no tumor growth in I.3 treated animals. It was statistically significant in all I.3 applied groups sing from week 2 of the whole experiment. The effect was independent of the application route (intraperitoneal or subcutaneous) and of the dose in this application.

In contrast to I.3, cisplatin was ineffective in the management of SK-N-AS neuroblastoma and showed no significant activity.

The anticancer activity of I.3 as a typical representative of this generation of betulinines was demonstrated under in vivo conditions. This novel compound seems to be highly active against human neuroblastoma under in vivo conditions. Together with its broad anticancer activity and novel, previously unidentified mechanism of action, the compounds of the present invention are believed to be of therapeutic potential for cancer patients in the future.

11.4. Betulinine I.3 induces rapid dephosphorylation of Rb Protein and Apontosis Related Caspase Activation.

As discussed earlier, the G1/S transition is tightly regulated by phosphorylation of retinoblastoma protein (Rb).

Since Rb protein contains multiple phosphorylation sites for CDKs, its phosphorylated form has molecular weight about 110 kDa, while the molecular weight of hypophosphorylated protein is only 105 kDa. This small difference in molecular weight is enough to separate both forms by conventional SDS-PAGE electrophoresis.

CEM cells were cultured in Dulbeco's modified essential medium with 4.5 g dextrose/l, 10% of foetal calf serum, 2 mM glutamine, 100 U/ml penicillin and 100 µg/ml streptomycin with/without below indicated concentrations of betulinic acid (BA) or I.3. At selected time points, cells were harvested, washed in ice cold Hank's balanced salt solution and solubilized on ice using the SDS-PAGE sample buffer containing protease and phosphatase inhibitors (10 µg/ml of leupeptin, 10 µg/ml of aprotinin-10 µg/ml of soybean trypsin inhibitor, 100 µmol of benzamide, 1 mM of sodium vanadate, 1 mM of NaF, 1 mM of phenylphosphate) and boiled immediately.

Total cellular proteins (100 µg/well) were separated on SDS-PAGE electophoresis, blotted on polyvinyldifluoride membranes and total Rb protein, including proteolytic fragment(s) were detected using a pRb monoclonal antibody (Oncogene, Germany, Rb(Ab-5), Cat# OP66 Rev 02-Sep.-96 EB, Clone LM95.1) and visual by chemiluminiscence (ECL-Western Blotting System, Amersham). Details of the Western blot technique are described in Ausubel, F. M., Brent, R., Kingston, R. E., Moore, D. D., Seidman, J. G., Smith, J. A., Struhl, K (Eds): Short Protocols in Molecular Biology, 2nd edition, John Wiley & Sons, New York, Chichester, Brisbane, Toronto, Singapore, 1992, page 10-33-10-35.

Figure 3:
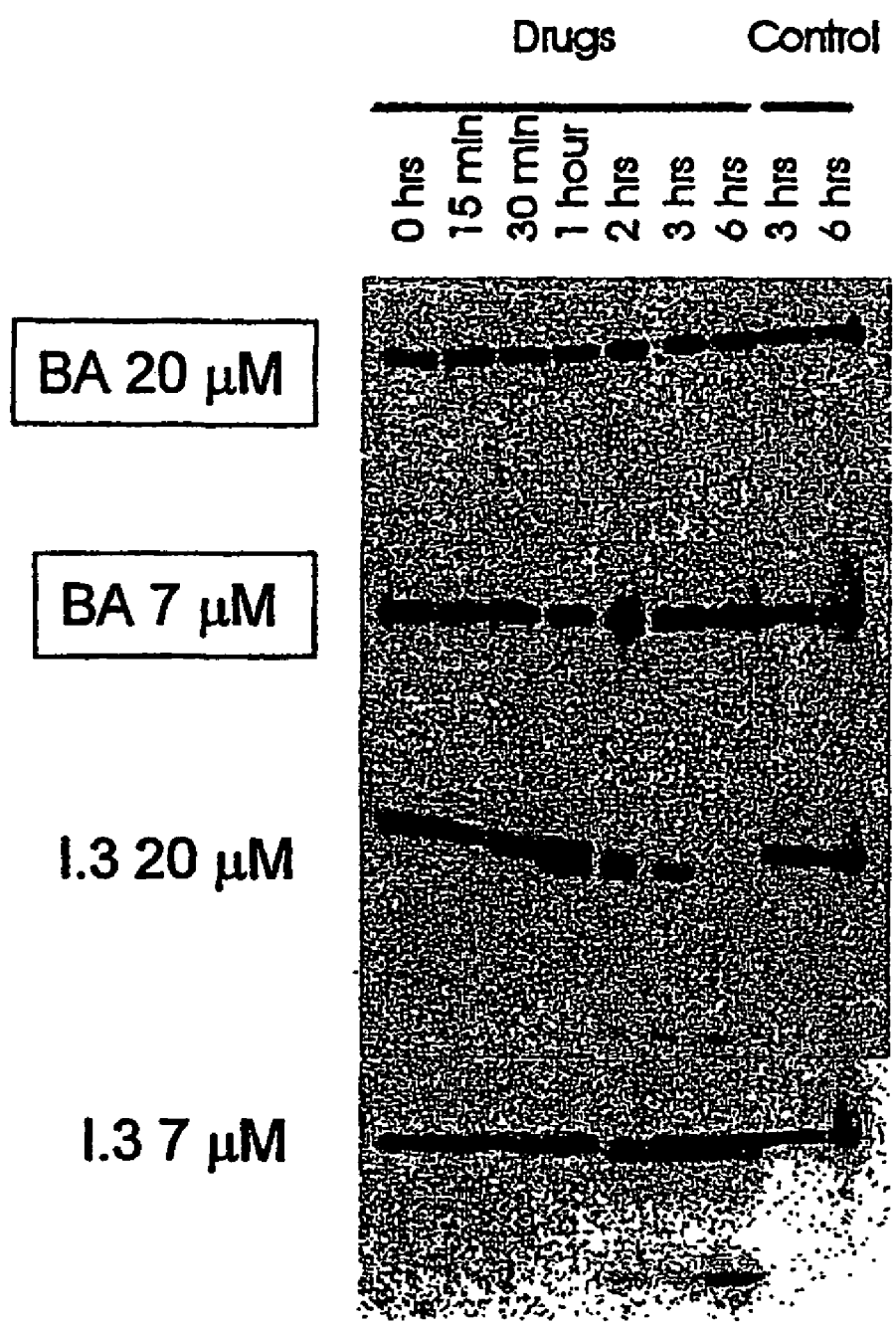
FIG. 3 shows the results of SDS-PAGE electrophoresis of total cellular proteins. In particular, the gel shows that betulinine I.3, but not betulinic acid (BA) induces rapid dephosphorylation of Rb protein.

The results of this study indicate that in CEM lymphoblastic leukaemia cells, Rb protein is rapidly dephosphorylated following treatment with I.3, but not betulinic acid (FIG. 3).

This is demonstrated by a shift of Rb protein mass from the hyperphosphorylated form with a molecular mass of about 110 kDa to the hypophosphorylated form (105 kDa). The effect of I.3 is time and concentration dependent; at 20 μM concentration, the hypocoincident form of Rb appears as early as 15 minutes after the treatment, while at 7 μM the same effect appears after 2 hours. Interestingly, cleavage of the Rb protein after hypophosphorylation was accompanied with the disappearance of a 105 kDa Rb and the appearance of an immunoreactive fragment of Rb protein with molecular weight about 42 kDa. According to the literature, proteolytic decomposition of Rb is a typical hallmark of apoptosis due to activation of cellular caspases.

The results of this study clearly indicate that the betulinines of the present invention, but not betulinic acid itself are capable of inducing the rapid dephosphorylation of key cell cycle regulatory protein Rb. This is followed by the induction of apoptosis, which has been reported to activate cellular caspases. Activated caspases have the capacity to cleave target proteins, including Rb. This is illustrated by the time and concentration dependent appearance of an immunoreactive fragment of Rb protein with molecular weight 42 kDa in I.3 treated cells.

11.5. Betulinine I.3 Induces G1 Block and Apoptosis in Tumour Cells.

Hypophosphorylation of Rb protein is accompanied with cell cycle block on the G1/S transition. To investigate whether incubation of tumour cells with betulinines will result in cell cycle block and/or apoptosis, a flow-cytometry study was performed with measurement of total DNA content in CEM cells treated with/without I.3. Taxol (paclitaxel) was used as a positive control, since this drug is known to result in the cumulation of cells in the G2 phase.

Figure 4A:
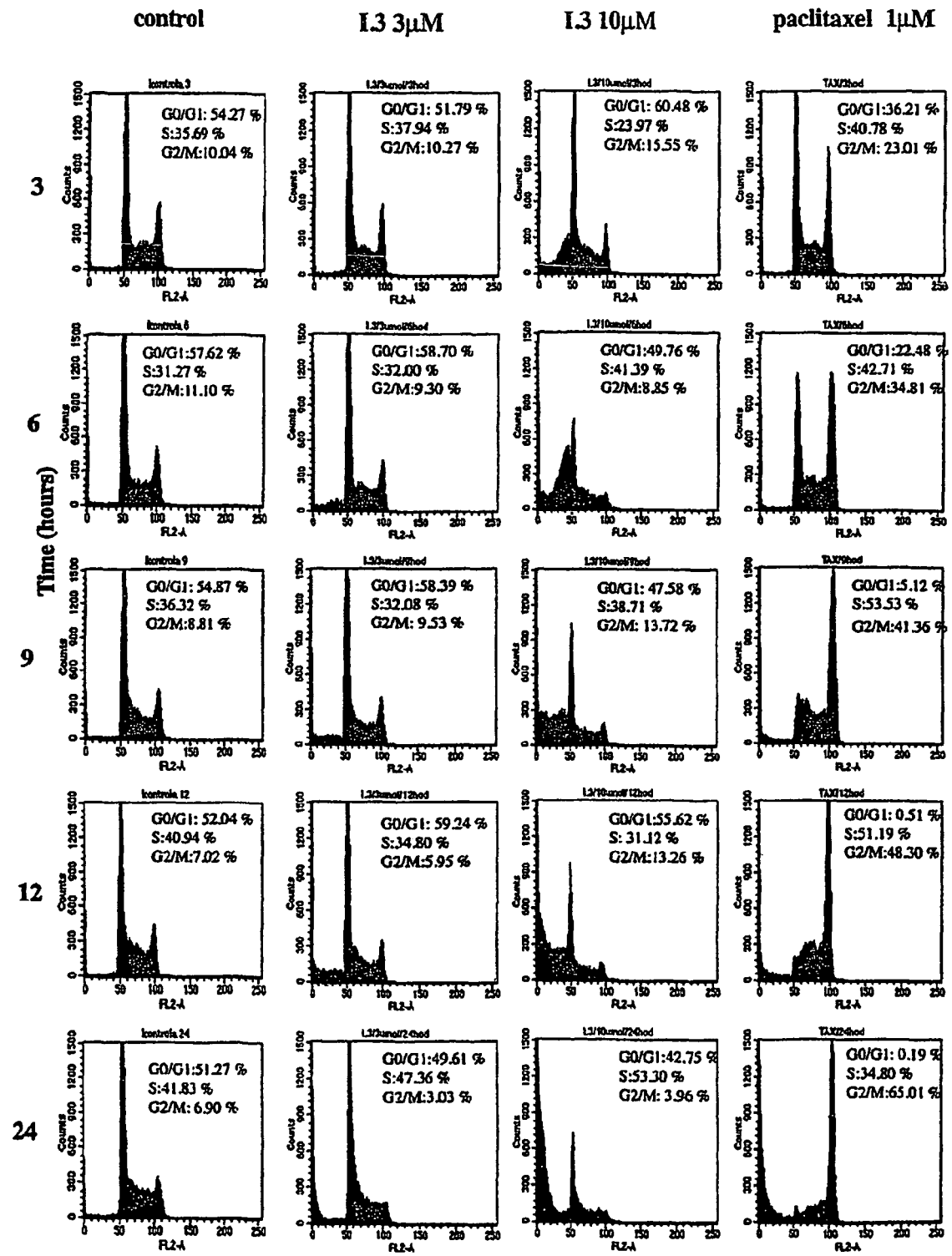
FIG. 4A shows a cell cycle analysis of cells treated with I.3 and paclitaxel as a control.
Figure 4B:
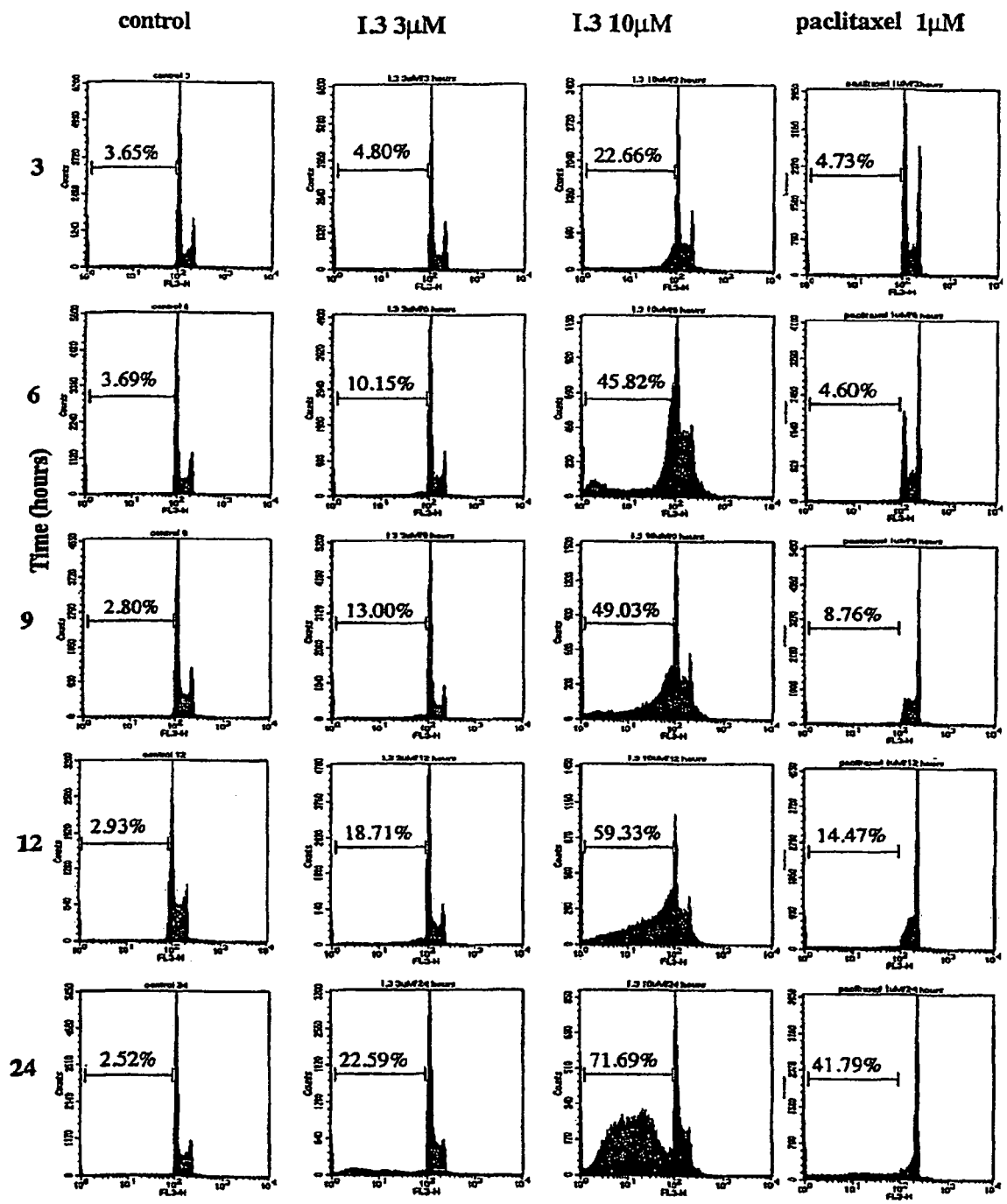
FIG. 4B shows the induction of apoptosis in cells treated with I.3 or paclitaxel as a control.

Briefly, CEM cells were cultured in Dulbeco's modified essential medium with 4.5 g dextrose/l 10% of foetal calf serum, 2 mM glutamine, 100 U/ml penicillin and 100 μg/ml streptomycin with/without the indicated concentrations of paclitaxel or I.3 (FIG. 4A). At selected time points, cells were harvested, washed in ice cold Hank's balanced salt solution (HBSS) and fixed in 70% ethanol at −20° C. overnight. The next day, ethanol was removed by centrifugation, cells were washed twice in HBSS and a cellular pellet ($10^6$ cells) was reconstituted in staining solution (propidium iodide 60 μg/ml, DNA-se free RNA-se 175 U/ml in HBSS) for 15 minutes at 37° C. The DNA content of individual cells was analyzed on flow cytometer Excalibur (Becton and Dickinson) at excitation wavelength of 488 nm.

As indicated in FIG. 4A, B I.3 induces cumulation of cells in G0/G1 phases of the cell cycle, which is accompanied by rapid apoptosis (appearance of sub-G1 cells). The effect is concentration and time dependent. Induction of G1 block and apoptosis is consistent with dephosphorylation of Rb protein 11.6. Betulinine I.3 Induces Rapid Histone Acetylation.

Cellular cytotoxicity studies (data not shown) demonstrated that the cytotoxic activity of I.3 strongly correlates with actinomycin D (p<0.00001). Since actinomycin D is a well known inhibitor of RNA polymerases, these results suggest that I.3 is targeting transcriptional complexes.

As discussed earlier, the G1/S transition is tightly regulated by phosphorylation of retinoblastoma protein (Rb). Hypophosphorylated Rb silences specific genes that are active in the S phase of the cell cycle and which are regulated by E2F transcription factors. Rb binds to the active domain of E2F and then actively repress the promoter by a mechanism that is poorly understood. Recent studies show that Rb associates with a histone deacetylase (HDAC 1 and 2) through the Rb pocket domain. Rb recruits histone deacetylase to E2F and thus Rb cooperates with HDAC to repress the E2F-regulated promotor of the gene. Inhibition of histone deacetylase activity by specific inhibitor trichostatin A (TSA) inhibits Rb-mediated repression of a E2F transcriptional activity.

In order to provide the evidence of interference of betulinines with transcription, the ability of I.3 to modify histone acetylation was investigated.

CEM cells were cultured in Dulbeco's modified essential medium with 4.5 g dextrose/l, 10% of foetal calf serum, 2 mM glutamine, 100 U/ml penicillin and 100 μg/ml streptomycin with/without the indicated concentrations of HDAC inhibitor TSA or I.3. At selected time points, cells were harvested, washed in ice cold Hank's balanced salt solution and solubilized on ice using SDS-PAGE sample buffer containing protease and phosphatase inhibitors (10 μg/ml of leupeptin, 10 μg/ml of aprotinin, 10 μg/ml of soybean trypsin inhibitor, 100 μmol of benzamide, 1 mM of sodium vanadate, 1 mM of NaF, 1 mM of phenylphosphate) and boiled immediately.

Total cellular proteins (100 μg/well) were separated on SDS-PAGE electrophoresis, blotted on polyvinyldifluoride membranes and acetylated histone was detected using a anti-acetyl(Lys9)-histone H3 rabbit polyclonal antibody (Cell Signalling Technology, Beverly, Mass.; Cat# 9671L) and visualized by chemiluminiscence (ECL-Western Blotting System, Amersham). Details of the Western blot technique are described in Ausubel, F. M., Brent, R., Kingston, R. E., Moore, D. D., Seidman, J. G., Smith, J. A., Struhl, K (Eds): Short Protocols in Molecular. Biology, 2nd edition, John Wiley & Sons, New York, Chichester, Brisbane, Toronto, Singapore, 1992, page 10-33-10-35.

The results of this study indicate that in CEM lymphoblastic leukaemia cells, H3 histone is rapidly acetylated in Lys9 position following the treatment of both TSA and betulinine I.3 (FIG. 5). The effect of I.3 is time and concentration dependent; at 20 μM ($10 \times IC_{50}$) acetylated histone appears as soon as 30 minutes after incubation. Interestingly, CEM cells cultured with 2 μM of I.3 ($IC_{50}$) show histone acetylation in time points in between 45-120 minutes, which is consistent with degradation half-life of I.3 under in vitro conditions (data not shown). On the other hand, however, TSA at 0.24 μM ($IC_{50}$) showed no significant ability to increase histone acetylation, suggesting that mechanism(s) of cytotoxic activity of TSA may be more complex that we originally realised.

The results of this study clearly indicate that the betulinines of the present invention, are capable of inducing the rapid histone acetylation. It is generally accepted that N termini of core histones are central to the processes that modulate nucleosome structure. Hyperacetylation of the histones reduces their ability to constrain the path of DNA within chromatin, resulting in allosteric changes in nucleosomal conformation, destabilization of internucleosomal contacts, and an increase in the accessability of nucleosomal DNA to transcription factors. The amount of histone acetylation is determined by an equilibrium between histone acetyltransferases (HAT) and histone deacetylases (HDAC). The balance plays an important role in the regulation of gene transcription as well as the genesis or suppression of cancer. Unfortunately, the question of whether betulinines inhibit HDAC directly or indirectly remains open. As discussed earlier, betulinines induce rapid dephosphorylation of Rb protein. Hypophosphorylated Rb was shown to bind both HDAC and E2F-DP1 complex. It has been recently reported that E2F-1, -2, and -3, but not E2F-4, -5, and -6, associate with and are acetylated by p300 and cAMP-response element-binding protein acetyltansferases. Acetylation occurs at three conserved lysine residues located at the N-terminal boundary of their DNA binding domains. Acetylation of E2F-1 in vitro and in vivo markedly increases its binding affinity for a consensus E2F DNA-binding site, which is paralleled by enhanced transactivation of an E2F-responsive promoter. Acetylation of E2F-1 was reversed by HDAC1, indicating that reversible acetylation is a mechanism for regulation also of non-histone proteins. Thus, inhibition of HDAC by synthetic compounds should result in both histone and transcription factor acetylation resulting in transcriptional activation of responsive genes. Interestingly, a number of oncosuppressors and virus promotor driven genes are transcritionally repressed in cancer/transfected/virus infected cells due to constitutive deacetylation of specific promoters. Inhibition of HDAC results in re-activation of onco-suppressors and genes under virus promotor. Those skilled in the art will recognise that betulinines could be used not only in treatment of cancer, but also in the treatment of diseases or in therapeutic approaches, where transcriptional repression of specific gene (s) is undesired, for instance transcriptional silencing of vectors used in gene therapy.

Notably, since these potential drugs do not exhibit any CDK inhibitory activity (data not shown), we expect that they possess a new, previously unreported mechanism of action.

Those skilled in the art will recognise, or be able to ascertain using no more than routine experimentation, many equivalents to the specific embodiments of the invention described herein. Such equivalents are intended to be encompassed by the claims.

The invention claimed is:

1. A method of treating a proliferative disease selected from cancer and leukemia, said method comprising administering a therapeutically effective amount of a compound of formula I, or a pharmaceutically acceptable salt thereof

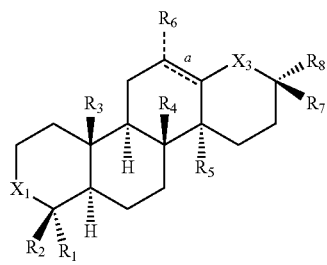

I wherein:
 $X^1$ is C=O, C=NOR$^{1a}$, CHOR$^{1a}$, CHOCOR$^{1a}$, CHOCOY-Hal, CHOC(O)OR$^9$, CHOC(O)OR$^{1a}$, CHOC(O)OR$^{10}$, and Hal is Br, Cl, I, F;
 $X^3$ and $R^8$ together are CHOCOCH$_2$ and form a cyclic lactone;
 $R^{1-5}$ are each independently H or lower alkyl;
 $R^6$ is H or absent if "a" is a double bond;
 $R^7$ is H, COOR$^{1c}$, YOCOR$^{1c}$, COOYOCOR$^{1e}$, YCOOR$^{1e}$;
 $R^9$ is an OH-substituted alkyl group, an ether group or a cyclic ether;
 $R^{10}$ is lower alkyl substituted Hal;
 "a" is a double bond or single bond;
 and wherein Y=(CH$_2$)$_n$
 n=0 to 5;
 $R^{1a}$, $R^{1c}$ and $R^{1e}$ are each independently H or lower alkyl.

2. The method of claim 1, wherein $X^1$ CHOR$^{1a}$, CHOCOR$^{1a}$ or CHOCOY-Hal.

3. The method of claim 1, wherein:

$R^{2-5}$ are all methyl and $R^1$ is H or C$_{1-4}$ alkyl;
 $X^1$ is —CHOCOCH$_2$, —CHOH or —CHOCOCH$_3$ and
 $R^7$ is H, COOH, COOMe, CH$_2$OAc, COOYOCOR$^{1e}$ or YCOOR$^{1e}$ where Y is CH$_2$ and R$^{1e}$ is C$_{1-4}$ alkyl.

4. The method of claim 3, wherein R$^7$ COOYOCOR$^{1e}$ or YCOOR$^{1e}$ where Y is CH$_2$ and R$^{1e}$ is methyl or butyl.

5. The method of claim 1, wherein "a" is a single bond and $R^6$ is H.

6. A method of treating a proliferative disease selected from cancer and leukemia, said method comprising administering a compound of formula I, or a pharmaceutically acceptable salt thereof,

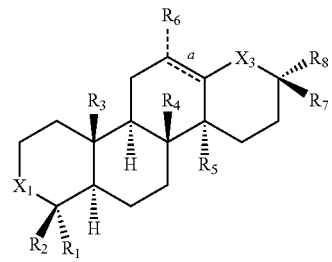

wherein the compound is selected from the group consisting of:

| No. | $X^1$ | $R^1$ | $X^3$ | a | $R^{2-5}$ | $R^6$ | $R^7$ | $R^8$ |
|---|---|---|---|---|---|---|---|---|
| 1.55 | CHOAc | CH$_3$ | ① | single | Me | H | H | ① |
| 1.56 | CHOH | CH$_3$ | ① | single | Me | H | H | ① | where:
① means cyclic five-membered lactone from $X^3$ to $R^8$:CHOCOCH$_2$.

7. A method of preparing a pharmaceutical composition comprising admixing a compound of formula I, as defined in claim 1, and a pharmaceutical carrier, excipient or diluent.

8. A compound of the formula Ia, or a pharmaceutically acceptable salt thereof;

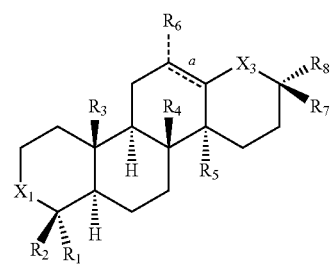

Ia wherein:
 $X^1$ is C=O, C=NOR$^{1a}$, CHOR$^{1a}$, CHOCOY-Hal, CHOC(O)OR$^9$, CHOC(O)OR$^{1a}$ or CHOC(O)OR$^{10}$, and Hal is Br, Cl, I, F;
 $X^3$ and $R^8$ together are CHOCOCH$_2$ and form a cyclic lactone;
 $R^{1-5}$ are each independently H or lower alkyl;
 $R^6$ is H or absent if "a" is a double bond;
 $R^7$ is H, COOR$^{1c}$, YOCOR$^{1c}$, COOYOCOR$^{1e}$, YCOOR$^{1e}$;
 $R^9$ is an OH-substituted alkyl group, an ether group or a cyclic ether;

$R^{10}$ is lower alkyl substituted Hal;

"a" is a double bond or single bond;

and wherein $Y=(CH_2)_n$ n=0 to 5;

$R^{1a}$, $R^{1c}$ and $R^{1e}$ are each independently H or lower alkyl.

9. The compound of claim 8, wherein $X^1$ is $CHOR^{1a}$ or CHOCOY-Hal.

10. The compound of claim 8, wherein:

$R^{2-5}$ are all methyl and $R^1$ is H or methyl; and $X^1$ is —CHOCOCH$_2$Cl or —CHOH.

11. The compound of claim 8, wherein $R^7$ is $COOYOCOR^{1e}$, $YCOOR^{1e}$, where Y is $CH_2$ and $R^{1e}$ is methyl or butyl.

12. The compound of claim 8, wherein "a" is a single bond and $R^6$ is H.

13. A compound of formula Ia, or a pharmaceutically acceptable salt thereof

Ia wherein the compound is selected from the group consisting of:

| No. | $X^1$ | $R^1$ | $X^3$ | a | $R^{2-5}$ | $R^6$ | $R^7$ | $R^8$ |
|-----|-------|-------|-------|---|-----------|-------|-------|-------|
| 1.55 | CHOAc | CH$_3$ | ← | single | Me | H | H | ← |
| 1.56 | CHOH | CH$_3$ | ← | single | Me | H | H | ← | where:

←means cyclic five-membered actone from $X^3$ to $R^8$: CHOCOCH$_2$.

14. A compound of the formula Ib, or a pharmaceutically acceptable salt thereof;

Ib wherein:

$X^1$ is C=O, C=NOR, $CHOR^{1a}$, $CHOCOR^{1a}$, CHOCOY-Hal, $CHOC(O)OR^9$, $CHOC(O)OR^{1a}$ or $CHOC(O)OR^{10}$, and Hal is Br, Cl, I, F;

$X^3$ $R^8$ together are CHOCOCH$_2$ and form a cyclic lactone;

$R^{1-5}$ are each independently H or lower alkyl;

$R^6$ is H or absent if "a" is a double bond;

$R^7$ is H, $COOR^{1c}$, $YOCOR^{1c}$, $COOYOCOR^{1e}$, $YCOOR^{1e}$;

$R^9$ is an OH-substituted alkyl group, an ether group or a cyclic ether;

$R^{10}$ is lower alkyl substituted Hal;

"a" is a double bond or single bond;

and wherein $Y=(CH_2)_n$ n=0 or 2 to 5;

$R^{1a}$, $R^{1c}$ and $R^{1e}$ are the same or different groups of $R^1$, or a pharmaceutically acceptable salt thereof.

15. The compound of claim 14, wherein $X^1$ $CHOR^{1a}$, $CHOCOR^{1a}$ or CHOCOY-Hal.

16. The compound of claim 14, wherein:

$R^{2-5}$ are all methyl and $R^1$ is H or methyl; and $X^1$ is —CHOCOCH$_2$Cl, —CHOH or —CHOCOCH$_3$.

17. The compound of claim 14, wherein $R^7$ is $COOYOCOR^{1e}$, $YCOOR^{1e}$, where Y is $CH_2$ and $R^{1e}$ is methyl or butyl.

18. The compound of claim 14, wherein "a" is a single bond and $R^6$ is H.

* * * * *